United States Patent [19]

Pasteris

[11] Patent Number: 4,802,911

[45] Date of Patent: Feb. 7, 1989

[54] PHENYL-SUBSTITUTED SULFONAMIDES

[75] Inventor: Robert J. Pasteris, Wilmington, Del.

[73] Assignee: E. I. Du Pont de Nemours and Company, Wilmington, Del.

[21] Appl. No.: 63,218

[22] Filed: Jun. 17, 1987

Related U.S. Application Data

[63] Continuation of Ser. No. 705,833, Mar. 1, 1985, which is a continuation-in-part of Ser. No. 607,990, May 7, 1984, abandoned.

[51] Int. Cl.$^4$ .................... A01N 43/54; A01N 43/72; C07D 239/42; C07D 417/12

[52] U.S. Cl. ........................................... 71/92; 71/90; 71/91; 574/321; 574/331; 574/332; 574/49

[58] Field of Search ............... 71/92, 90, 91; 544/321, 544/331, 332, 49

[56] References Cited

U.S. PATENT DOCUMENTS

| | | | |
|---|---|---|---|
| 4,586,950 | 5/1986 | Pasteris | 71/93 |
| 4,589,911 | 5/1986 | Ehrenfreund et al. | 71/91 |
| 4,634,465 | 1/1987 | Ehrenfreund et al. | 71/90 |

Primary Examiner—John M. Ford

[57] ABSTRACT

This invention relates to novel condensed ring sulfonylureas and their use as herbicides and growth regulants.

27 Claims, No Drawings

PHENYL-SUBSTITUTED SULFONAMIDES

This application is a continuation of my copending application, U.S. Ser. No. 705,833, filed Mar. 1, 1985, which is a continuation-in-part of my then copending application, U.S. Ser. No. 607,990, filed May 7, 1984, now abandoned.

BACKGROUND OF THE INVENTION

This invention relates to novel condensed ring sulfonylureas and their use as herbicides and growth regulants.

U.S. Pat. No. 4,127,405 teaches compounds which are useful for controlling weeds in wheat having the formula:

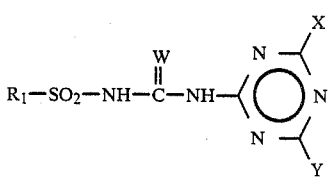

wherein
$R_1$ is

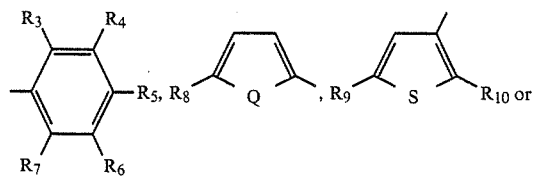

$R_3$ and $R_6$ are independently hydrogen, fluorine, chlorine, bromine, iodine, alkyl of 1-4 carbon atoms, alkoxy of 1-4 carbon atoms, nitro trifluoromethyl, cyano, $CH_3S(O)_n$— or $CH_3CH_2S(O)_n$—;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1-2 carbon atoms or alkoxy of 1-2 carbon atom;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1-3 carbon atoms, trifluoromethyl, $CH_3S$— or $CH_3OCH_2$—; and Y is methyl or methoxy; or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

French Pat. No. 1,468,747 discloses the following para-substituted phenylsulfonamides, useful as antidiabetic agents:

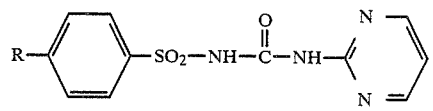

wherein
R=H, halogen, $CF_3$ or alkyl.

Logemann et al., Chem. Ab., 53, 18052g (1959), disclose a number of sulfonamide, including uracil derivatives and those having the formula:

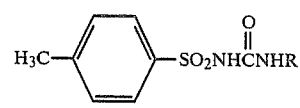

wherein
R is butyl, phenyl or

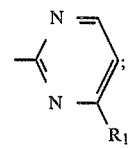

and
$R_1$ is hydrogen or methyl.

When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121-5 (1962) [Chem. Ab., 59 1633 e] describes the synthesis of N-[(2,6-dimethoxypyrimidin-4-yl)aminocarbonyl]-4-methylbenzenesulfonamide:

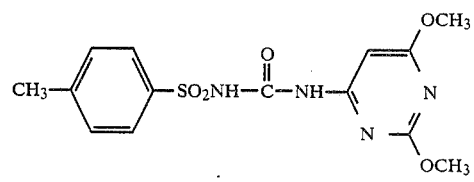

Based upon similarity to a known compound, the author predicted hypoglycemic activity for the foregoing compound.

Netherlands Pat. No. 121,788, published Sept. 15, 1966, teaches the preparation of compounds of Formula (i), and their use as general or selective herbicides,

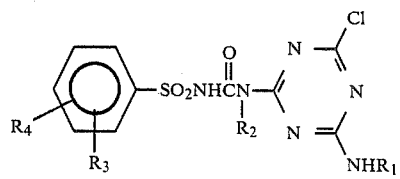

wherein $R_1$ and $R_2$ may independently be alkyl of 1-4 carbon atoms; and $R_3$ and $R_4$ may independently be hydrogen, chlorine or alkyl of 1-4 carbon atoms.

Compounds of formula (ii), and their use as antidiabetic agents, are reported in *J. Drug. Res.* 6, 123 (1974).

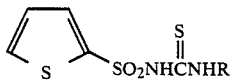
(ii)

wherein R is pyridyl.

U.S. Pat. No. 4,169,719 discloses herbicidal benzenesulfonylureas.

Herbicidal indanesulfonylureas are taught in EP-A-82,681, published June 29, 1983.

Herbicidal quinolinesulfonylureas are described in U.S. Pat. No. 4,369,329, issued Jan. 18, 1983.

Herbicidal benzofuran, benzothiophene, benzopyran and benzothiopyran sulfonylureas are disclosed in EP-A-79,683, published May 25, 1983.

EP-A-82,681, published June 29, 1983, discloses herbicidal 1,3-benzodioxole and 1,4-benzodioxanesulfonylureas.

South African patent application No. 835165 discloses herbicidal sulfonylureas of the general structure shown below:

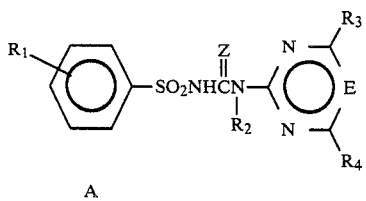

A wherein A is an unsubstituted or substituted bridge of 3 or 4 atoms which contains 1 or 2 oxygen, sulfur or nitrogen atoms and, together with the linking carbon atom, forms a non-aromatic 5- or 6-membered heterocyclic ring system, with the proviso that two oxygen atoms are separated by at least one carbon atom and that oxygen and sulfur atoms are only linked to each other if the sulfur atom takes the form of the —SO— or SO₂— group.

South African patent application No. 837,434 discloses herbicidal sulfonamides of formula

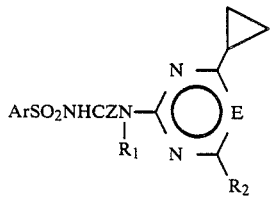

where
Ar is

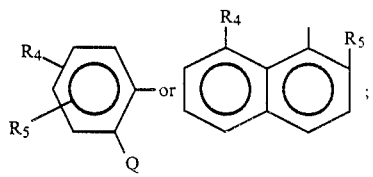

and $R_2$ is halogen, $C_1$-$C_3$ alkyl, $C_1$-$C_3$ haloalkyl, $C_1$-$C_3$ alkoxy, $C_1$-$C_3$ haloalkoxy, amino, $C_1$-$C_3$ alkylamino, di($C_1$-$C_3$ alkyl)amino, $C_3$-$C_6$ cycloalkyl or $C_2$-$C_6$ alkoxyalkyl.

SUMMARY OF THE INVENTION

This invention relates to novel compounds of Formula I, agriculturally suitable compositions containing them, and their method-of-use as pre-emergent or post-emergent herbicides or plant growth regulants.

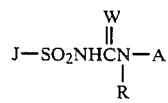
I wherein
J is

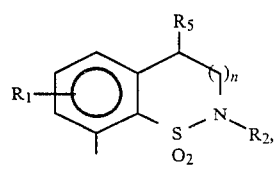
$J_1$

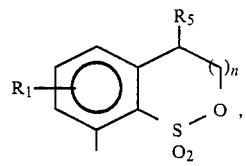
$J_2$

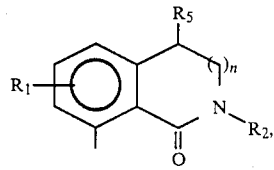
$J_3$

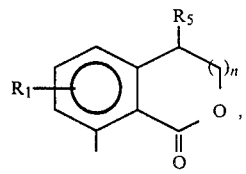
$J_4$

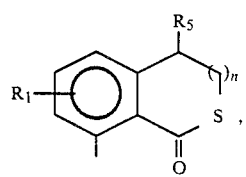
$J_5$

-continued
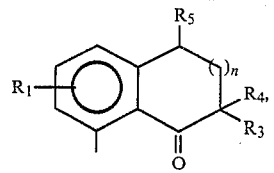 J6
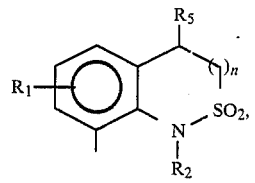 J7
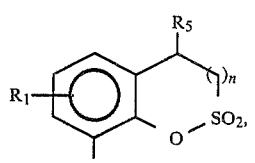 J8
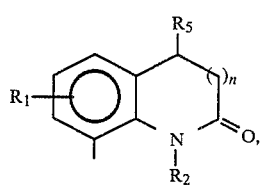 J9
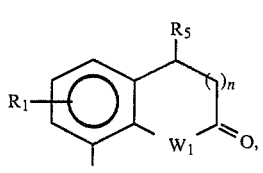 J10
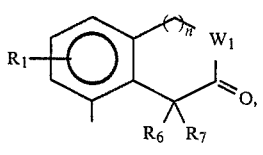 J11
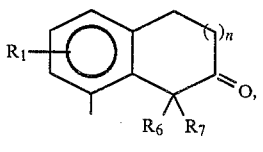 J12
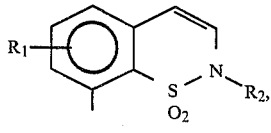 J13
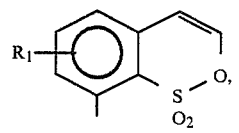 J14
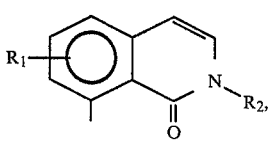 J15
-continued
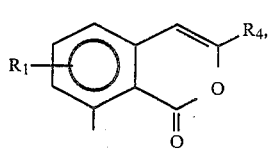 J16
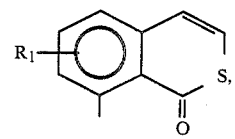 J17
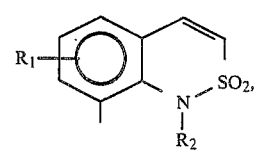 J18
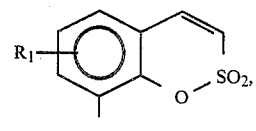 J19
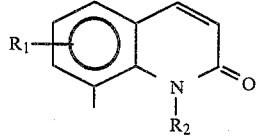 J20
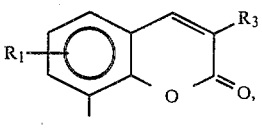 J21
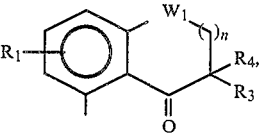 J22
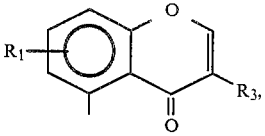 J23
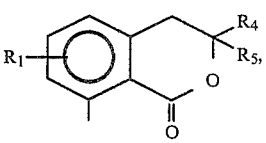 J24
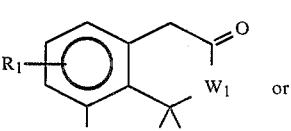 J25 or -continued

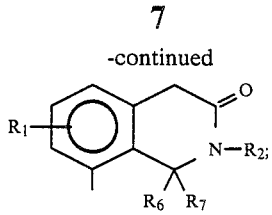

$J_{26}$ n is 0, 1 or 2;
W is O or S;
$W_1$ is O or S;
R is H or $CH_3$;
$R_1$ is H, F, Cl, Br, $CH_3$, $OCH_3$, $CF_3$, $SCH_3$ or $OCF_2H$;
$R_2$ is H or $C_1-C_4$ alkyl;
$R_3$ and $R_4$ are independently H, $C_1-C_4$ alkyl, Cl or Br;
$R_5$ is H or $CH_3$;
$R_6$ is H or $CH_3$;
$R_7$ is H or $CH_3$;
A is

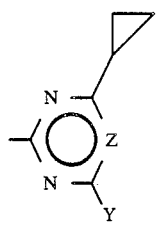

Y is
 $CH_3$, $CH_2CH_3$, $OCH_3$, $OCH_2CH_3$, $CH_2OCH_3$, $OCF_2H$, $SCF_2H$, $OCH_2CF_3$, $CF_3$, $OCH_2CH=CH_2$, $OCH_2C\equiv CH$, $NHCH_3$, $N(CH_3)_2$ or $CH(OCH_3)_2$: and
Z is CH or N; provided that
 (a) when W is S, then R is H;
 (b) the total number of carbon atoms in $R_3$ and $R_4$ is less than or equal to 4;
 (c) when $R_5$ is $CH_3$, then n is O;
 (d) when J is $J_{24}$, then $R_4$ and $R_5$ are not both H and $R_4$ is not Cl or Br;
 (e) when Y is $OCF_2H$, then Z is CH;
and their agriculturally suitable salts.

Preferred for reasons of their higher herbicidal activity, greater plant growth regulant activity or more favorable ease of synthesis are:

(1) Compounds of Formula I where W is O, $R_3$ and $R_4$ are independently H or $C_1-C_3$ alkyl and $R_1$ is bonded to the ortho or meta position of the ring relative to the sulfonylurea moiety.

(2) Compounds of Preferred 1 where $R_1$ is H, F, Cl, Br, $CH_3$, $OCH_3$, $CF_3$ or $SCH_3$ and R is H.

(3) Compounds of Preferred 2 where $R_1$ is H, F, Cl, $CH_3$, $OCH_3$ or $SCH_3$, $R_5$ is H and Y is $CH_3$, $OCH_3$ or $CH_2OCH_3$.

(4) Compounds of Preferred 3 where J is $J_1$.
(5) Compounds of Preferred 3 where J is $J_2$.
(6) Compounds of Preferred 3 where J is $J_3$.
(7) Compounds of Preferred 3 where J is $J_4$.
(8) Compounds of Preferred 3 where J is $J_5$.
(9) Compounds of Preferred 3 where J is $J_6$.
(10) Compounds of Preferred 3 where J is $J_7$.
(11) Compounds of Preferred 3 where J is $J_8$.
(12) Compounds of Preferred 3 where J is $J_9$.
(13) Compounds of Preferred 3 where J is $J_{10}$.
(14) Compounds of Preferred 3 where J is $J_{11}$.
(15) Compounds of Preferred 3 where J is $J_{12}$.
(16) Compounds of Preferred 3 where J is $J_{13}$.
(17) Compounds of Preferred 3 where J is $J_{14}$.
(18) Compounds of Preferred 3 where J is $J_{15}$.
(19) Compounds of Preferred 3 where J is $J_{16}$.
(20) Compounds of Preferred 3 where J is $J_{17}$.
(21) Compounds of Preferred 3 where J is $J_{18}$.
(22) Compounds of Preferred 3 where J is $J_{19}$.
(23) Compounds of Preferred 3 where J is $J_{20}$.
(24) Compounds of Preferred 3 where J is $J_{21}$.
(25) Compounds of Preferred 3 where J is $J_{22}$.
(26) Compounds of Preferred 3 where J is $J_{23}$.
(27) Compounds of Preferred 3 where J is $J_{24}$.
(28) Compounds of Preferred 3 where J is $J_{25}$.
(29) Compounds of Preferred 3 where J is $J_{26}$.

DETAILED DESCRIPTION OF THE INVENTION

Synthesis

The following discussion represents a general outline for the preparation of the compounds of this invention. All of the syntheses described below are multistep with one or more methods being taught for each step. This allows for a wide variety of possible synthetic pathways to prepare a particular compound of Formula I. The proper choice of the synthetic pathway and the best ordering of the reaction sequences for each individual compound will be known to one skilled in the art.

The compounds of Formula I can be prepared by one or more of the methods described below in Equations 1 through 5.

As shown in Equation 1, many of the compounds of Formula I where J is other than $J_6$, $J_{12}$, $J_{22}$ and $J_{23}$, can be prepared by reacting a sulfonylisocyanate (W=O) or a sulfonylisothiocyanate (W=S) of Formula II with an appropriate heterocyclic amine of Formula III. R, A and W are as previously defined.

Equation 1

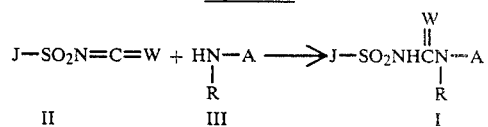

The reaction is carried out at 25° to 100° C. in an inert, aprotic solvent such as methylene chloride or xylene for 0.5 to 24 hours as taught in U.S. Pat. No. 4,127,405.

Compounds of Formula I, where W is S and R is H, (Ia) can be prepared by reacting the appropriate sulfonamide of Formula IV with a heterocyclic isothiocyanate of Formula V, as shown in Equation 2.

Equation 2

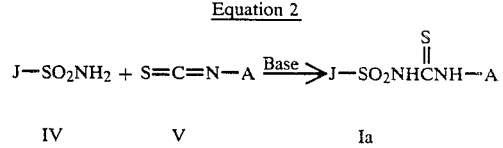

The reaction is carried out at 25° to 80° C. in an inert, aprotic solvent such as acetone or acetonitrile in the presence of a base such as potassium carbonate for 0.5 to 24 hours. The required heterocyclic isothiocyanates V are prepared from the corresponding amines III as taught in EPO Publication 35893.

Compounds of Formula I, where W is O (Ib), can be prepared by reacting a sulfonylcarbamate of Formula VI with an appropriate amine of Formula III, as shown in Equation 3.

Equation 3

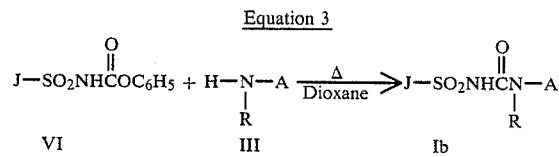

The reaction is carried out at 50° to 100° C. in a solvent such as dioxane for 0.5 to 24 hours as taught in EPO Publication No. 44807. The required carbamates VII are prepared by reacting the corresponding sulfonamides IV with diphenylcarbonate in the presence of a strong base.

Compounds of Formula Ib can also be prepared, as shown in Equation 4, by reacting a heterocyclic carbamate of Formula VII with an appropriate sulfonamide of Formula IV.

Equation 4

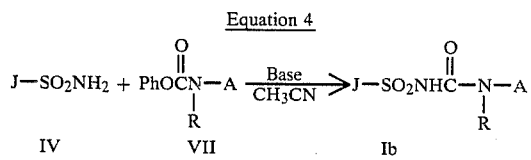

The reaction is carried out at 0° to 50° C. in a solvent such as acetonitrile or dioxane in the presence of a non-nucleophilic base such as DBU for 0.2 to 24 hours as taught in South African patent application No. 830441. The required phenylcarbamate VII are prepared by reacting the corresponding heterocyclic amines III with diphenylcarbonate or phenylchloroformate in the presence of a strong base.

Compounds of Formula Ib where J is other than $J_4$, $J_5$, $J_{10}$, $J_{11}$, $J_{16}$, $J_{17}$, $J_{21}$, $J_{24}$ and $J_{25}$ can be prepared by reacting the sulfonamides of Formula IV with an appropriate methylcarbamate of Formula VIII in the presence of an equimolar amount of trimethylaluminum, as shown in Equation 5.

Equation 5

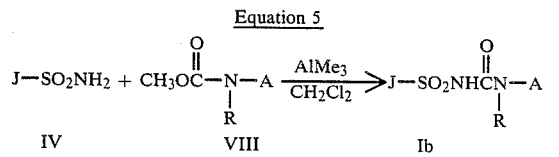

The reaction is carried out at 25° to 40° C. in a solvent such as methylene chloride for 10 to 96 hours under an inert atmosphere as taught in EPO No. 84,244 (7/27/83). The required carbamates VIII are prepared by reacting the corresponding amines III with diemthylcarbonate or methyl chloroformate in the presence of a strong base.

The intermediate sulfonylisocyanates (W=O) and sulfonylisothiocyanates (W=S) of Formula II from Equation 1 can be prepared as shown in Equations 6 through 8.

As shown in Equation 6, sulfonylisocyanates of Formula IIa where J is other than $J_6$, $J_{12}$, $J_{22}$ and $J_{23}$ can be prepared by the reaction of sulfonamides of Formula IV with phosgene, in the presence of n-butyl-isocyanate and a tertiary amine catalyst, at reflux in a solvent such as xylene by the method of U.S. Pat. No. 4,238,621.

Equation 6

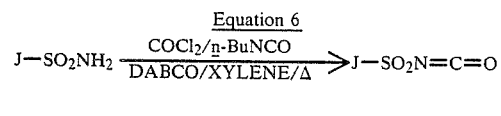

The sulfonylisocyanates can also be prepared from the sulfonamides by a two step procedure involving (a) reacting the sulfonamides with n-butyl-isocyanate in the presence of a base such as $K_2CO_3$ at reflux in an inert solvent such as 2-butanone forming a n-butylsulfonylurea; and (b) reacting this compound with phosgene and a tertiary amine catalyst at reflux in xylene solvent. The method is similar to a procedure taught by Ulrich and Sayigh, *Newer Methods of Preparative Organic Chemistry*, Vol. VI, p. 223–241, Academic Press, New York and London, W. Foerst Ed.

Alternatively, as shown in Equation 7, many of the sulfonylisocyanates of Formula IIa can be prepared by reacting the corresponding sulfonyl chlorides IX with cyanic acid salts.

Equation 7

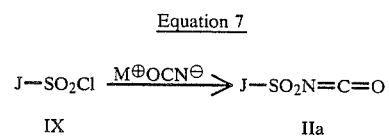

The reaction is carried out at 25° to 100° C. in an inert aprotic solvent such as acetonitrile for 0.5–24 hours in the presence of phosphorus pentoxide and an alkali metal salt such as lithium iodide according to the teachings of Japanese Pat. No. 76/26,816 (*Chem. Abst.*, 85: 77892e (1976)).

The sulfonylisothiocyanates of Formula IIb where J is other than $J_6$, $J_{12}$, $J_{22}$ and $J_{23}$ can be prepared, as shown in Equation 8, by contacting the sulfonamides of Formula IV with carbon disulfide in the presence of two equivalents of a strong base. The resulting salt is then reacted with phosgene according to the teachings of K. Hartke, *Arch. Pharm.*, 299, 174 (1966).

Equation 8

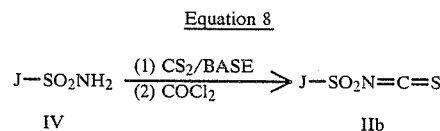

The sulfonamides of Formula IV of Equations 2, 4, 5, 6 and 8 can be prepared from the corresponding sulfonyl chlorides of Formula IX by contacting with either anhydrous or aqueous ammonia as shown in Equation 9.

Equation 9

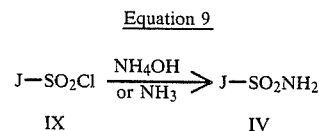

The preparation of sulfonamides from sulfonyl chlorides is widely reported in the literature, for reviews see: F. Hawking and J. S. Lawrence, "The Sulfonamides," H. K. Lewis and Co., London, 1950 and E. H.

Northey, "The Sulfonamides and Allied Compounds," Reinhold Publishing Corp., New York, 1948.

Alternatively, many sulfonamides IV can be prepared by dealkylation of their corresponding N-t-butyl sulfonamides X as shown in Equation 10.

Equation 10

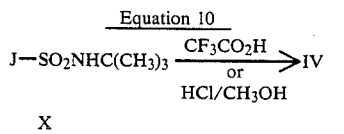

The reaction is carried out by contacting the N-t-butyl sulfonamide X with a strong acid such as trifluoroacetic acid or methanolic HCl at 25° to 50° C. for 0.5 to 24 hours. The N-t-butyl sulfonamides X are readily prepared by reacting sulfonylchlorides IX with t-butylamine and are useful either as an aid in purification, to enhance solubility for subsequent reactions such as Equation 12 below or to protect the sulfonamide function from competing with reactions at other parts of the molecule. An example of this would be conversion of X where J is $J_1$ and $R_2$ is H to X where J is $J_1$ and $R_2$ is other than H.

The unsaturated sulfonamides of Formula IVa can be prepared from the corresponding saturated sulfonamides of Formula IVb by the two step procedure shown in Equation 11. $G_1$-$G_2$ is $SO_2$—$NR_2$, $SO_2$—O, CO—$NR_2$, CO—O, CO—S, $NR_2$—$SO_2$, O—$SO_2$, $NR_2$—CO and O—CO, $R_1$ and $R_2$ are as previously defined and R′ is H or $C(CH_3)_3$.

Equation 11

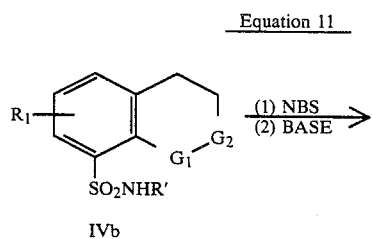

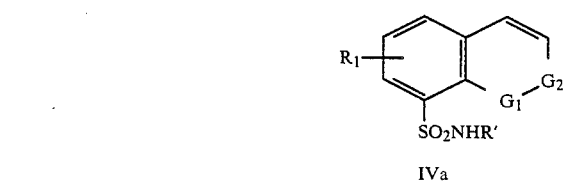

The first step involves benzylic bromination by N-bromosuccinimide to give a monobromide which is subsequently dehydrobrominated in a second step by reaction with a suitable base such as triethyl amine or potassium-t-butoxide in an inert solvent such as THF. This method has been used to prepare isocoumarins from 3,4-dihydroisocoumarins, see R. Barry, Chem. Rev., 64, 229 (1964). In cases where $R_1$ is an alkyl group, competitive bromination at this site may occur resulting in a mixture. The desired bromide may be separated at this stage, or after treatment with the base, by standard methods. A similar method may be used to prepare sulfonamides where J is $J_{23}$ from sulfonamides where J is $J_{22}$ (n=1).

The sulfonyl chlorides of Formula IX of Equations 7 and 9 are important intermediates for the preparation of the compounds of this invention. The synthesis of the required sulfonyl chloride intermediates are described in Equations 12 through 14.

As shown in Equation 12, many of the sulfonyl chlorides of Formula IX can be prepared from the corresponding amines XI.

Equation 12

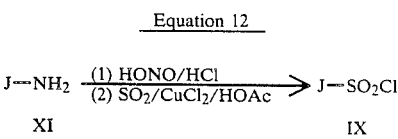

The reaction involves diazotization of the amine XI with sodium nitrite in HCl, followed by reaction of the diazonium salt with sulfur dioxide and cupric chloride in acetic acid analogous to the teachings of Yale and Sowinski, J. Org. Chem., 25, 1824 (1960).

Alternatively, sulfonyl chlorides of Formula IX can be prepared by a modification of the above procedure whereby the diazotization reaction is carried out in dilute sulfuric acid and the resulting diazonium salt is reacted with sulfur dioxide, HCl and cupric chloride in a cosolvent mixture consisting of acetic acid-water (1:1) and an immiscible, inert solvent such as 1-chlorobutane or methylene chloride at 0°-40° C. for 1 to 24 hours.

Many of the sulfonyl chlorides of Formula IX can also be prepared by oxidative chlorination of the corresponding thio compounds of Formula XII as shown in Equation 13. R′ is H, alkyl, benzyl or carbamoyl, $R_1$ is not $SCH_3$, $W_1$ is O and J does not contain nonaromatic unsaturation.

Equation 13

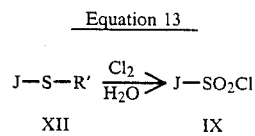

The reaction is carried out by addition of molecular chlorine or a chlorine equivalent to the thio compound in the presence of water at 0° to 80° C. in an aliphatic carboxylic acid solvent such as acetic acid or an inert organic solvent such as dichloroethane for 1 to 24 hours.

Alternatively, many of the sulfonyl chlorides of Formula IX can be prepared by the two-step sequence shown in Equation 14 starting from the thio compounds XII where R′ is H (XIIa), $R_1$ is not $SCH_3$ and $W_1$ is O.

Equation 14

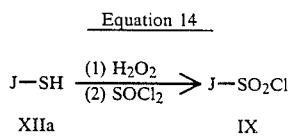

The thiol XII (R′=H) is contacted with excess hydrogen peroxide in the presence of base to give a sulfonic acid salt which in turn is converted to the desired sulfonyl chloride by contacting with a suitable reagent such as thionyl chloride or phophorous pentachloride as known to one skilled in the art.

Some of the sulfonyl chlorides of Formula IX may best be prepared by direct chlorosulfonation depending on the substitution pattern on the ring and the nature of the substituent as will be known to one skilled in the art.

Many of the S-arylthiocarbamates of Formula XIIb (XII, R'=CON(CH₃)₂) can be prepared by the Newman-Kwart rearrangement starting with the corresponding phenols XIII as shown in Equation 15.

Equation 15

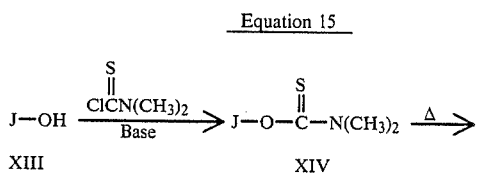

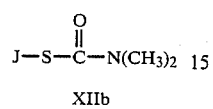

XIIb

The phenol XIII Is first converted to its corresponding O-aryl-N,N-dimethylthiocarbamoyl chloride in the presence of a base. The resulting O-aryl-N,N-dimethylthiocarbamate XIV is then heated at 150° C. to 300° C. for 2 to 24 hours as taught by Newman and Karnes *J. Org. Chem.*, 31, 3980 (1966) to give the desired S-aryl-N,N-dimethylcarbamate XIIb. The related thiols XIIa can be obtained by hydrolysis of the thiocarbamates XIIb. Many of the sulfides of Formula XII where R' is alkyl or benzyl can be prepared by reacting a halocompound of Formula XV with an appropriate mercaptan in the presence of a base as shown in Equation 16. R' is alkyl or benzyl and X is F, Cl or Br.

Equation 16

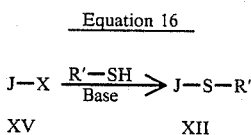

The reaction is carried out in a solvent such as DMF at 25° to 150° C. for 0.5 to 24 hours. The halo-compounds XV must not contain functionality which can be attacked by a mercaptide anion as will be known to one skilled in the art.

Many of the thiocompounds XII of Equation 13 and the chlorocompounds XV (X=Cl) of Equation 16, where J is J₁ and n is O, can be prepared by the reaction sequence shown in Equation 17. G is Cl or S-alkyl, R₁ does not contain Br, and R₅ is as previously defined.

Equation 17

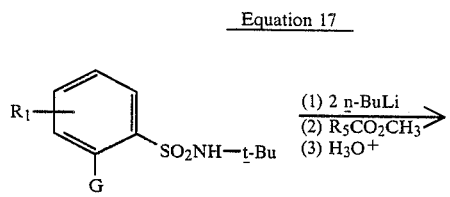

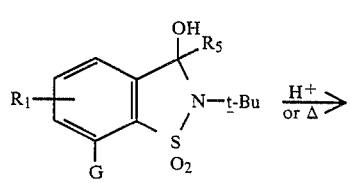

-continued
Equation 17

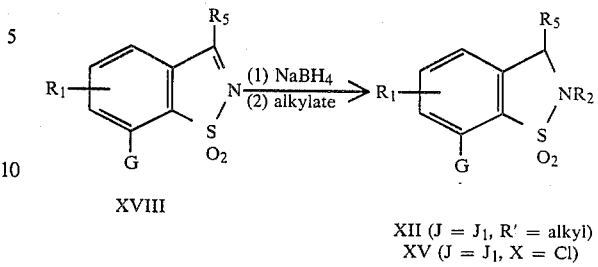

XVIII

XII (J = J₁, R' = alkyl)
XV (J = J₁, X = Cl)

The sequence begins by contacting an appropriately substituted N-t-butylbenzenesulfonamide XVI with two equivalents of butyl lithium at 0° to 25° C. in an inert solvent such as THF for 2 to 10 hours to give a dianion according to the teachings of J. Lombardino, *J. Org. Chem.*, 36, 1843 (1971). The dianion can then be trapped with an ester or, when R₅ is H, with dimethylformamide at −78° to 25° C. to produce, upon aqueous acid workup, the hemiaminal XVII. The hemiaminal XVII can be de-t-butylated and dehydrated by a catalytic amount of acid such as p-toluenesulfonic acid in a solvent such as benzene or toluene at reflux. The resulting benzisothiazole XVIII can be reduced with a reagent such as sodium borohydride in a suitable solvent such as ethanol to produce a 2,3-dihydrobenzisothiazole which is N-alkylated to give either XII (J=J₁, R'=alkyl) or XV (J=J₁, X=Cl) by standard methods known to one skilled in the art.

Many of the thio compounds XII of Equation 13 and the chloro compounds XV of Equation 16, where J is J₁ and n=1, can be prepared by the reaction sequence shown in Equation 18. G is Cl or S-alkyl, Y is H or CH₃, R₁ does not contain Br and R₂ is as previously defined.

Equation 18

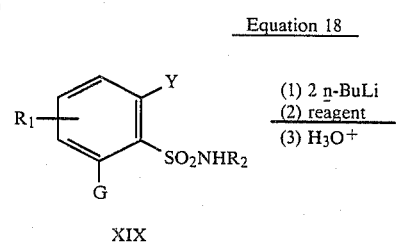

XIX

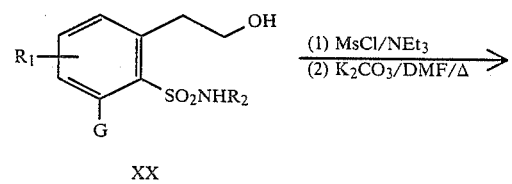

XX

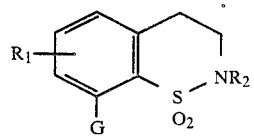

XII (J = J₁, R' = alkyl)
XV (J = J₁, X = Cl)

The reaction is carried out by reacting the N-substituted benzenesulfonamides XIX with two equivalents of n-BuLi at −78° to 25° C. in a solvent such as THF for 0.5 to 5 hours. When Y is H, an orthoanion is formed which is trapped with an appropriate epoxide to give the hydroxy sulfonamides XX. When Y is CH₃, an ortho methyl anion is produced which is reacted with an aldehyde or DMF to give alcohol XX. The alcohol can be mesylated by treatment of XX with mesyl chloride in the presence of an equivalent of a tertiary amine at 0° to 25° C. for 1 to 24 hours in a solvent such as methylene chloride. The resulting mesylate is cyclized by heating with a base such as potassium carbonate in a solvent such as DMF to produce the desired compounds XII ($J=J_1$, $R'$=alkyl) or XV ($J=J_1$, X=Cl). When $R_2$ is $C(CH_3)_3$, contacting with acid as described in Equation 10 will give the corresponding benzisothiazine where $R_2$ is H. This can be alkylated as described previously for the benzisothiazoles of Equation 17.

Many of the thio compounds of Formula XII, where $J=J_{24}$, can also be prepared from the thioether compounds XXI shown in Equation 19. Y is H or CH₃, $R_1$ does not contain Br, $R'$ is $C_2-C_4$ alkyl, $R_4$ is H or $C_1-C_4$ alkyl and $R_5$ is as previously defined.

Equation 19

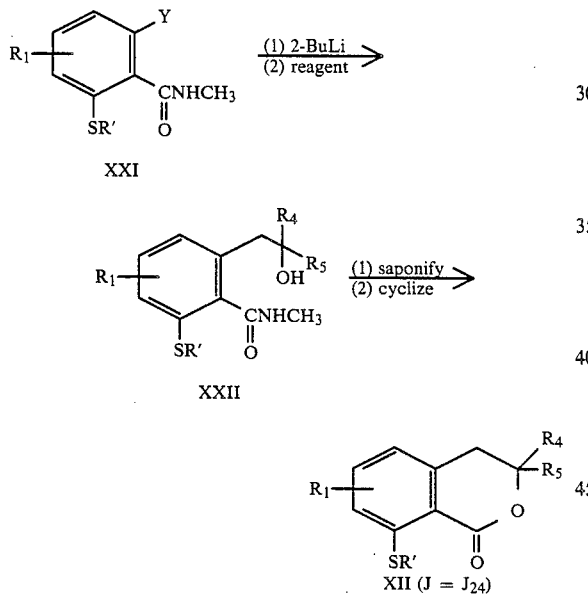

XXI

XXII

XII (J = J₂₄)

The reaction is carried out by reacting the N-methylcarboxamide XXI with two equivalents of n-BuLi at −78° to 25° C. in a solvent such as THF for 0.5 to 5 hours to give, when Y is H, an orthoanion which is trapped with an appropriate epoxide to give the hydroxy sulfonamides XXII as taught by Narasimkan and Bhide, *Chem. Comm.*, 1552 (1970). When Y is CH₃, an ortho methyl anion is produced which is reacted with an aldehyde or slowly enolizable ketones to give the amides XXII as taught by Watanabe et al. *Tetrahedron Lett.* 1647 (1982). The amides XXII are saponified by standard methods to the corresponding benzoic acids which readily cyclize upon heating in the presence of acid such as p-toluenesulfonic acid to give the desired lactones XII ($J=J_{24}$, $R'$=alkyl).

The amines of Formula XI in Equation 12, can be prepared by reduction of the corresponding nitro compounds of Formula XXIII, as shown in Equation 20.

Equation 20

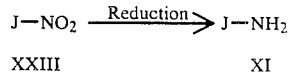

The reduction of nitro compounds to amines can be carried out by any of several known methods as described in *Preparative Organic Chemistry*, 4 Ed., p. 557–563, John Wiley and Sons, New York and London, G. Hilgetag and A. Martini Ed.

Many of the nitro compounds of Formula XXIII in Equation 20 can be prepared by the procedures outlined in Equations 21 through 47. With suitable modifications known to one skilled in the art, the general ring forming reactions outlined below for these nitrocompounds XXIII can be adapted to prepare phenols of Formula XIII and halocompounds of Formula XV.

As shown in Equation 21, many of the nitro compounds of Formula XXIII, where J is $J_1$ (XXIIIa) can be prepared starting from the appropriately substituted nitrobenzenes of Formula XXIV. $R'$ is H or $CH_2Cl$, $R_1$, $R_2$, $R_5$ and n are as previously defined.

Equation 21

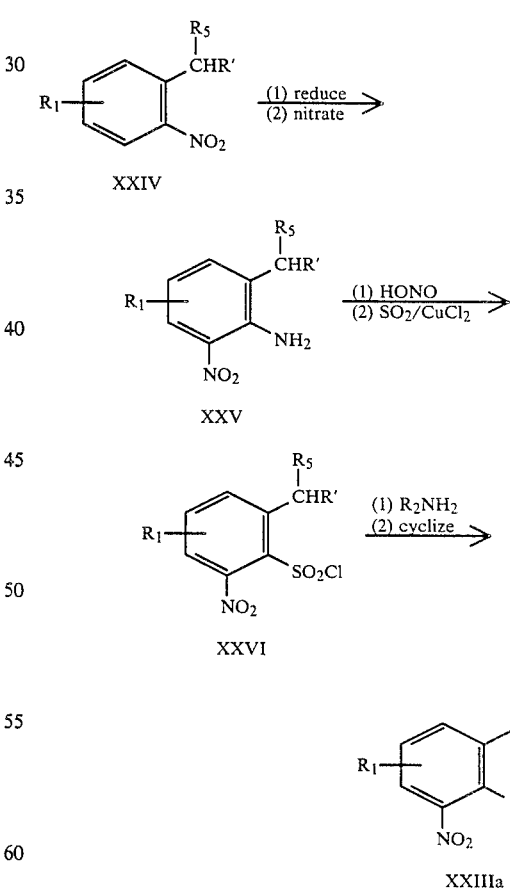

XXIV

XXV

XXVI

XXIIIa

The nitrobenzenes XXIV are first reduced to their corresponding amines and nitrated by standard methods to produce, in part, compounds of Formula XXV. In some instances, it may be desirable to first protect the amino group as its acetate prior to nitration as is known to one skilled in the art. The desired nitro compound XXV can be isolated by either fractional crystallization or chromatographic procedures and converted to sulfonyl chlorides XXVI by the method previously discussed in Equation 12. The intermediate sulfonyl chlorides XXVI can be converted into their corresponding sulfonamides by reaction with an appropriate amine (see Equation 9 for references) and subsequently cyclized (a) when R' is CH$_2$Cl, to the nitro-1,2-benzothiazines XXIIIa, where n is 1, by heating in the presence of a base such as potassium carbonate or (b) when R' is H, by contacting the sulfonamide with NBS in a solvent such as carbon tetrachloride to give sulfonamides where R' is Br, followed by contacting this product with a base to give the nitro benzisothiazoles XXIIIa where n is 0. (Note discussion of Equation 11 for NBS brominations when R$_1$ is alkyl.)

The procedure of Equation 21 is similar to the method taught by E. Sianesi et al., *Chem. Ber.*, 104, 1880 (1971) for the preparation of substituted 1,2-benzothiazine-1,1-dioxides. The starting nitrobenzenes XXIV can be prepared by standard methods known to one skilled in the art.

Alternatively, as shown in Equation 22, many of the nitro compounds of Formula XXIIIa where n is 1 can be prepared, in part, by contacting the nitro acetamides XXVII with fuming sulfuric acid according to the method taught by H. Zenno and T. Mizutani, Japanese Pat. No. 44/32,404 (1969) (*Chem. Abst.:* 72: 79122 (1970)) for the preparation of 7-nitro-1,2-benzothiazine-1,1-dioxide. The resulting benzothiazines can be isolated and subsequently alkylated by standard methods known to one skilled in the art.

Equation 22

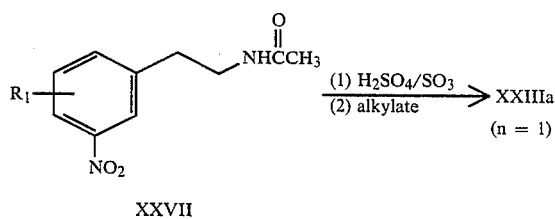

Many of the nitro compounds of Formula XXIIIa where n is 0 can also be prepared from the corresponding 1,2-benzisothiazoles XXVIII as shown in Equation 23. R$_1$, R$_2$ and R$_5$ are as previously defined.

Equation 23

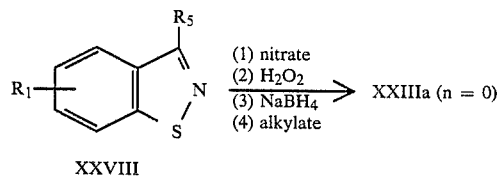

Nitration of XXVIII gives, in part, the 7-nitro derivative which is isolated by standard methods. The derivative is converted to its 1,1-dioxide by treatment with hydrogen peroxide. Reduction of the carbon-nitrogen double bond with NaBH$_4$ followed by alkylation of the resulting sulfonamide gives compounds XXIIIa where n is 0. The above reactions are characteristic of 1,2-benzisothiazoles XXVIII. For reviews of their synthesis and reactions, see L. L. Bambas, "The Chemistry of Heterocyclic Compounds," Vol. 4, part III, 1952, p. 223-378, and M. Davis, *Adv. Heterocyclic Chem.*, Vol. 14 (1972) p. 43-98. 1,2-Benzothiazines are also well known in the literature, for a review of their chemistry and alternate methods of their preparation see J. G. Lombardino, D. E. Kuhla, *Adv. Heterocyclic Chem.*, Vol. 28 (1981) p. 73-126.

As shown in Equation 24, many of the nitro compounds of Formula XXIIIb where J=J$_2$ can be prepared from the appropriately substituted nitro sulfonyl chlorides XXVI. R' is H or CH$_2$Cl, R$_1$, R$_5$ and n are as previously defined.

Equation 24

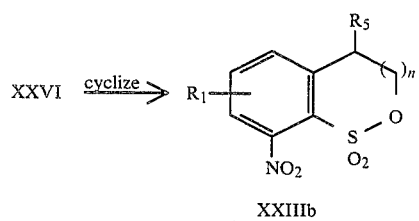

The nitro sulfonyl chlorides XXVI, previously described in Equation 21, can be (a) cyclized to the nitro benzoxathiins XXIIIb (n32 1) by heating in water at 50° to 100° C. for 0.1 to 1 hour when R' is CH$_2$Cl or (b) cyclized to the nitro benzoxathioles XXIII (n=0) by brominating with NBS or bromine (see discussion of Equation 11 for brominations when R$_1$ is methyl) followed by heating in water as described above. This is similar to the method taught by Clemo and Turnbull, *J. Chem. Soc.*, 124 (1947) for the preparation of substituted 2,1-benzoxathiins.

2,1-Benzoxathiins and 2,1-benzoxathioles are well known in the literature, for a review of their synthesis and reactions see *Chemistry of Heterocyclic Compounds*, Vol. 21, John Wiley and Sons, New York, 1966, part 2 and part 1, respectively.

As shown in Equation 25, many of the nitro compounds of Formula XXIII where J=J$_4$ (XXIIId) can be prepared from the appropriately substituted amines XXV. R' is H or CH$_2$Cl, R$_1$, R$_5$ and n are as previously defined.

Equation 25

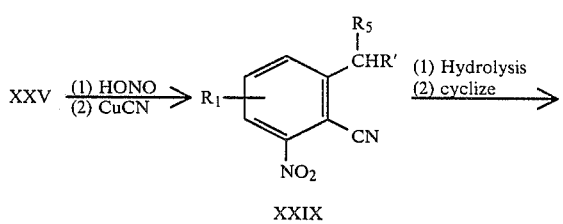

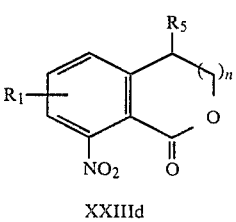

The nitro amines XXV, previously described in Equation 21, can be converted into the corresponding cyano compounds XXIX by the "Sandmeyer Reaction" (T. Sandmeyer, *Chem. Ber.*, 17, 1633, 2650 (1884)). The cyano function is hydrolyzed to a carboxylic acid by methods known to one skilled in the art, and the carboxylic acids or their corresponding esters can be (a) cyclized to the nitro isocoumarins XXIIId (n=1) by heating in the presence of base when R' is $CH_2Cl$, or (b) cyclized to the nitro phthalides XXIIId (n=0) when R' is H by first brominating with NBS or bromine (note discussion of Equation 11 for brominations when $R_1$ is methyl) followed by heating in a solvent such as aqueous dioxane. The latter method is that taught by J. A. Houbion et al., *Org. Prep. and Procedures Int.*, 11, 27 (1979) for the preparation of 7-nitrophthalide (XXIIId, n=0, $R_1$=H).

The procedure of Equation 25 is similar to the method of P. Banejce and D. Chaudhury, *J. Org. Chem.*, 26, 4344 (1961) for the preparation of substituted isocoumarins; similar methods can be utilized for the preparation of isocoumarins of the $J_{24}$ type. Isocoumarins are well known in the literature, for a review of their synthesis and reactions see R. Barry, *Chem. Rev.*, 64, 229–260 (1964).

Many of the nitro compounds of Formula XXIII, where n=0 can also be prepared by reduction of the corresponding 3-nitrophthalic anhydrides with either sodium borohydride or lithium aluminum hydride in tetrahydrofuran as taught by M. Kayser and P. Morand, *Can. J. Chem.*, 58, 2484 (1980) for the preparation of 7-nitrophthalide (XXIIId; n=0, $R_1$=H). Phthalides and phthalic anhydrides are well known in the art, for a review of their synthesis and reactions see, S. Wawzonek, *Heterocyclic Compounds*, Vol. 2, John Wiley and Sons, Inc., New York, 1951.

As shown in Equation 26, many of the nitro compounds of Formula XXIII where J is $J_5$ (XXIIIe) can be prepared from the appropriately substituted cyano compounds XXIX. R' is H or $CH_2Cl$, $R_1$, $R_5$ and n are as previously defined.

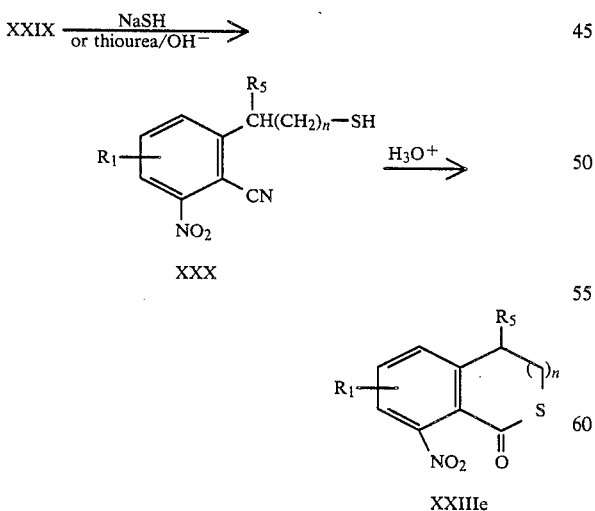

Equation 26

The nitrobenzonitriles XXIX, previously described in Equation 25, can be converted into mercaptans XXX by reacting compounds XXIX where R' is Br or $CH_2Cl$ with an alkali metal salt of hydrogen sulfide in a polar solvent such as ethanol or DMF according to the teachings of S. Gabriel and E. Leupold, *Chem. Ber.*, 31, 2646 (1898). The cyano mercaptans are cyclized to the thiol ethers by heating in aqueous acid as taught by M. Renson and R. Collienne, *Bull. Soc. Chem. Belqes*, 73, 491 (1964) for the preparation of 2-thiophthalide.

Alternatively, as shown in Equation 27, many of the nitro compounds of Formula XXIIIe can be prepared from the lactones of Formula XXIIId by reaction with potassium t-butyl mercaptide in a solvent such as DMF at 0° to 100° C. for 0.5 to 24 hours to give the carboxylic acids XXXI, which are then heated in the presence of a catalytic amount of an acid such as p-toluenesulfonic acid in a solvent such as xylene at 100° to 140° C. for 2 to 24 hours.

Equation 27

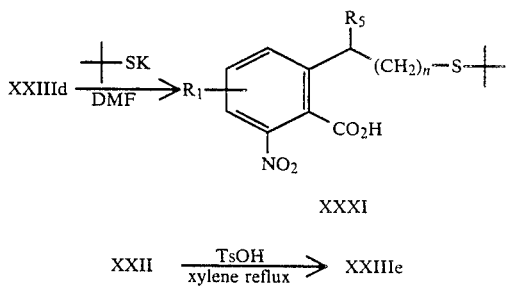

2-Thiophthalides are widely reported in the literature, for a review of their synthesis and reactions see, B. Iddon, *Adv. Heterocyclic. Chem.*, Vol. 14 (1972) pp. 368–381.

As shown in Equation 28, many of the nitro compounds of Formula XXIII, where J is $J_3$ (XXIIIc) can be prepared from the appropriately substituted benzonitriles XXIX. R' is H or $CH_2Cl$, $R_1$, $R_2$, $R_5$ and n are as previously defined.

Equation 28

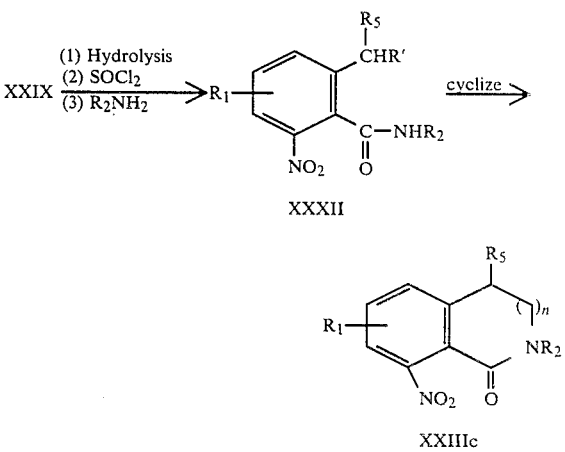

The benzonitriles XXIX, previously described in Equation 25, are hydrolyzed to carboxylic acids, converted to their corresponding acid chlorides by contacting with a reagent such as thionyl chloride and subsequently reacted with the appropriate amine, by standard methods, to give the amides XXXII. The intermediate amides XXXII can be cyclized to the nitro compounds XXIIIc by the procedures previously described in Equation 21 for converting sulfonamides of XXVI into nitro compounds XXIIIa.

Alternatively, many of the nitro compounds of Formula XXIIIc can be prepared from the nitro compounds of Formula XXIIId as shown in Equation 29. $R_1$, $R_2$, $R_5$ and n are as previously defined.

Equation 29

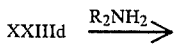

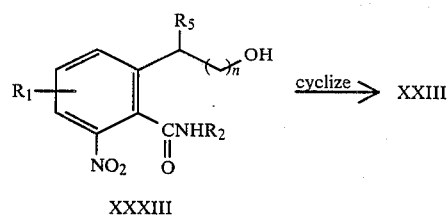

The reactions of phthalides with amines to produce phthalimidines is well known, see C. Hollins, *The Synthesis of Nitrogen Ring Compounds*, Ernest Benn Limited, London, 1924. In these reactions, heating the phthalides (XXIIId, n=0) with an amine produces the phthalimidines (XXIIIc, n=0) directly, the intermediate alcohols XXXIII (n=0) are not isolated. With the 3,4-dihydrocoumarins (XXIIId, n=1) the intermediate amide alcohols XXXIII (n=1) are formed (see P. Maitte, *Colloq. Intern. Centre Natl. Rech. Sci.* (Paris) 64, 197 (1955), *Chem. Abst.*, 55: 10426 (1961)) and can be converted to the dihydroisoquinolines XXIIIc (n=1) by first conversion to the corresponding mesylate followed by heating with a base as described above in Equation 18 for the preparation of compounds XII ($J=J_1$, $R'$=alkyl) and XV ($J=J_1$, X=Cl) from the sulfonamide alcohols XX. For a comprehensive review of the synthesis and reactions of dihydroisoquinolones see N. J. McCorkindale, *The Chemistry of Heterocyclic Compounds*, Vol. 38, part III, John Wiley and Sons, New York, in press.

As shown in Equation 30, many of the nitro compounds of Formula XXIII, where J is $J_6$ (XXIIIf) can be prepared, in part, by cyclization of the appropriate arylproprionic (n=0) or arylbutyric (n=1) acid chlorides XXXIV. $R_1$, $R_3$, $R_4$, $R_5$ and n are as previously defined.

Equation 30

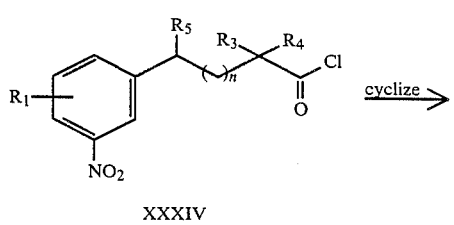

-continued
Equation 30

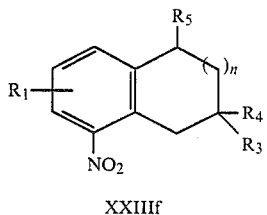

The reaction is carried out by heating the acid chloride with a typical Friedel-Crafts reagent such as aluminum chloride or stannic chloride. For a comprehensive review of this and related reactions, see "Friedel-Crafts and Related Reactions", Vols. 1–4, Interscience, New York and London, G. A. Olah, Ed. This procedure has been used to prepare a number of substituted-7-nitro-1-indanones (XXIIIf, n=0), see: H. Jones and T. Y. Shen, German Pat. Nos. 2,337,120 (1974) and Y. Takahi and Y. Yura, Japanese Pat. No. 78/12,421 (1978) *Chem. Abst.*, 89: 101857c.

Alternatively, many of the nitro compounds of Formula XXIIIf can be prepared by benzylic oxidation of the corresponding nitroindanes or nitrotetralines as taught by D. Biggs, et al., *J. Med. Chem.*, 19, 472 (1976) for the preparation of 8-nitrotetralone (XXIIIf, n=1, $R_1$, $R_3$, $R_4$ and $R_5$=H). Nitroindanes and nitrotetralines are well known in the literature and can be prepared by methods known to one skilled in the art.

Additionally, ketones of Formula XXIIIf where $R_3$ and/or $R_4$ are other than hydrogen can be prepared from ketones XXIIIf where $R_3$ and/or $R_4$ are hydrogen by standard ketone alkylation and halogenation methods. For a review, see: H. House, *Modern Synthetic Reactions*, 2nd Edition, W. A. Benjamin, Inc., Menlo Park, Calif., 1972, p. 542–570 and 459–478, respectively.

As shown in Equation 31, many of the nitro compounds of Formula XXIII where J is $J_7$ (XXIIIg) can be prepared from the appropriately substituted nitrobenzenes XXIV. $R'$ is Br or $CH_2Br$, $R_1$, $R_2$, $R_5$ and n are as previously defined.

Equation 31

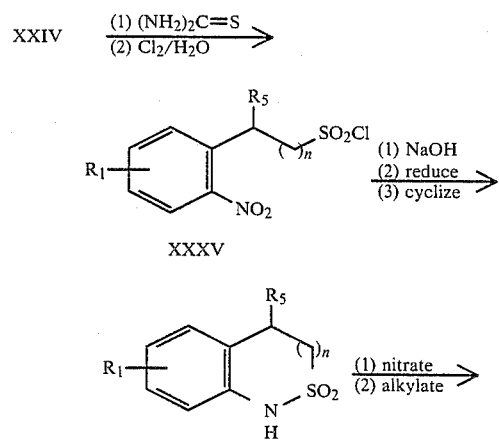

-continued
Equation 31

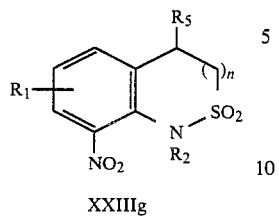

XXIIIg

-continued
Equation 32

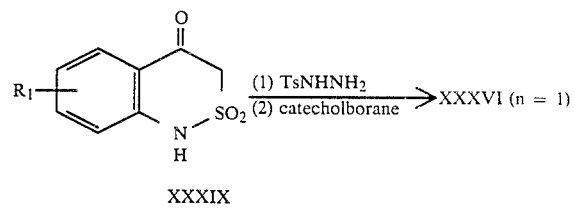

XXXIX

The nitrobenzenes XXIV, previously described in Equation 21, are heated with thiourea in a suitable solvent such as ethanol to give thiouronium salts which are oxidatively chlorinated in aqueous acetic acid to give the sulfonyl chlorides XXXV (see also discussion of Equation 13). The sulfonyl chlorides XXXV are dissolved in 10% aqueous sodium hydroxide solution and the nitro groups are catalytically hydrogenated to give intermediate amino sulfonate salts. The salts are cyclized with phosphorous pentachloride and acetyl chloride to give the sultams XXXVI according to the teachings of B. Loev and M. F. Kormendy, *J. Org. Chem.* 30, 3163 (1965) for the preparation of 3,4-dihydro-2,1-benzothiazine-2,2-dioxide (XXXVI, n=1, $R_1$, $R_5$=H).

Alternatively, the sulfonyl chlorides XXXV can be converted to their corresponding sulfonamides by the methods discussed in Equation 9. Reduction of the nitro group according to procedures of Equation 20 gives the corresponding amino sulfonamides which are cyclized to sultams XXXVI by heating, in the presence of HCl, according to the teachings of E. Sianesi, et al., *Chem. Ber.*, 104, 1880 (1971) for the preparation of 3,4-dihydro-2,1-benzothiazine-2,2-dioxide (XXXVI, n=1, $R_1$, $R_5$=H).

Many of the sultams XXXVI can be nitrated, in part, ortho to the ring nitrogen by standard methods known to one skilled in the art. Isolation by either fractional crystallization or chromatographic methods followed by alkylation of the ring nitrogen under standard conditions gives the nitrosultams XXIIIg as taught by E. Sianesi loc. cit. for the preparation of 1-methyl-8-nitro-3,4-dihydro-2,1-benzothiazine-2,2-dioxide (XXIIIg, n=1, $R_1$, $R_5$=H, $R_2$=$CH_3$).

Many of the sultams of Formula XXXVI of Equation 31 where n=1, can also be prepared from anilines XXXVII as shown in Equation 32. $R_1$ is as previously defined.

Equation 32

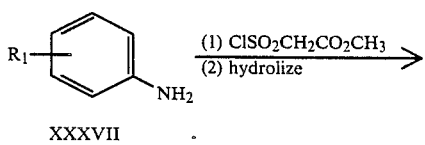

XXXVII

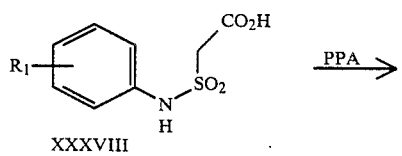

XXXVIII

The substituted anilines XXXVII are reacted with methyl chlorosulfonylacetate in the presence of an acid scavenger to give methyl sulfamoyl acetate intermediates which are hydrolized with dilute sodium hydroxide solution to the corresponding carboxylic acids XXXVIII. The carboxylic acids XXXVIII can be cyclized by heating with polyphosphoric acid to give the 4-benzothiazinones XXXIX as taught by B. Loev et al., *J. Org. Chem.*, 31, 3531 (1966) for the preparation of 4-keto-3,4-dihydro-2,1-benzothiazine-2,2-dioxide (XXXIX, $R_1$=H). When $R_1$ is meta to nitrogen, cyclization may produce an isomeric mixture. The desired compounds XXXIX can be isolated by either fractional crystallization or chromatographic methods known to one skilled in the art. The benzothiazines XXXVI (n=1) are prepared by reducing the tosylhydrazone derivative of ketones XXXIX with catecholborane in a solvent such as chloroform for 2 to 24 hours at ambient temperatures according to the teachings of G. Kabalka and J. Chandler, *Synthetic Commun.*, 9, 275 (1979).

The synthesis and chemistry of 2,1-benzothiazines has been reviewed, see J. G. Lombardino and D. E. Kuhla, *Adv. Heterocyclic Chem.*, Vol. 28 (1981) p. 73–126. Additionally, for a review of the synthesis and chemistry of benzothiazinone dioxides, see P. Catsoulacos and Ch. Camoutsis, *J. Heterocyclic Chem.*, 16, 1503 (1979).

As shown in Equation 33, many of the nitro compounds of Formula XXIII where J is $J_8$ (XXIIIh) can be prepared from the appropriately substituted nitrophenols XXXX. R' is Br or $CH_2Cl$, $R_1$, $R_5$ and n are as previously defined.

Equation 33

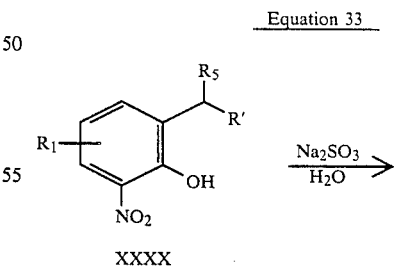

XXXX

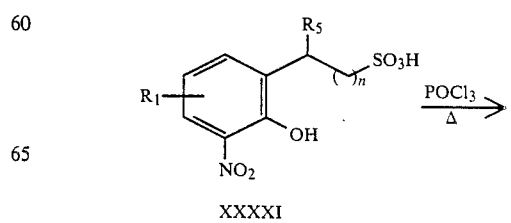

XXXXI

-continued
Equation 33

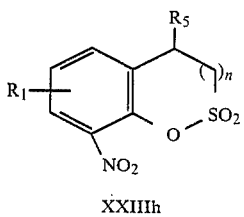

XXIIIh

The nitrophenols XXXX, prepared by methods known to one skilled in the art, are heated with aqueous sodium sulfite to give the sulfonic acids XXXXI which are then cyclized by heating with phosphorous oxychloride.

The method is similar to those taught by Marckwald and Frahne, *Chem. Ber.* 31, 1854 (1898) for the preparation of 1,2-benzoxathiole, and Truce and Hoerger, *J. Amer. Chem. Soc.*, 76, 5357 (1954) and 77 2496 (1955) for the preparation of 1,2-benzoxathiin.

Alternatively, many 1,2-benzoxathioles can be prepared from phenols XXXXII by the sequence shown in Equation 34. This is the method taught by Shearing and Smiles, *J. Chem. Soc.*, 1348 (1937) for the preparation of 5-methyl-1,2-benzoxathiole, nitration gives, in part, compounds of Formula XXIIIh. For a review of this and alternate methods of synthesis of 1,2-benzoxathioles, see *Chemistry of Heterocyclic Compounds*, Vol. 21, part 1 (1966).

Equation 34

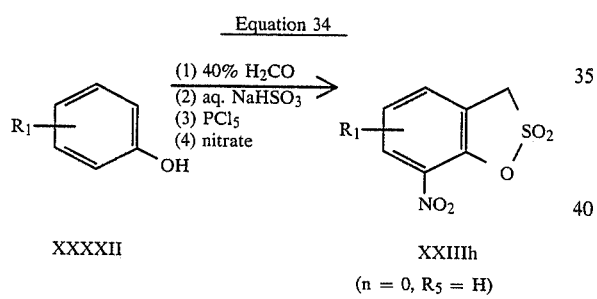

XXXXII         XXIIIh
               ($n = 0$, $R_5 = H$)

Many compounds of Formula XXIIIh where $n=1$ can be prepared from nitrophenols XXXX where $R'=R_5=H$ by the three step sequence shown in Equation 35.

Equation 35

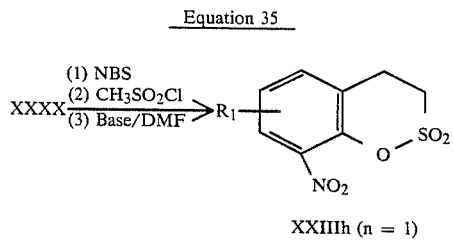

XXIIIh ($n = 1$)

The phenol is brominated with NBS in a solvent such as carbon tetrachloride and the hydroxy group is then converted to its methanesulfonate ester by treatment with mesyl chloride in the presence of an acid scavenger such as triethylamine in a solvent such as methylene chloride. The methanesulfonate ester is then cyclized by reacting with a strong base such as sodium hydride or potassium t-butoxide in a polar solvent such as DMF at 0° to 80° C. for 0.5 to 24 hours. For alternative methods of synthesis and the reactions of 1,2-benzoxathiins, see *Chemistry of Heterocyclic Compounds*, Vol. 21, part 2, (1966).

As shown in Equation 36, many of the nitro compounds of Formula XXIII where J is $J_9$ (XXIIIi) can be prepared from the appropriately substituted nitrobenzenes XXIV. R' is Br or $CH_2Br$. $R_1$, $R_2$, $R_5$ and n are as previously defined.

Equation 36

XXIV $\xrightarrow[\text{(2) Hydrolyze}]{\text{(1) KCN}}$

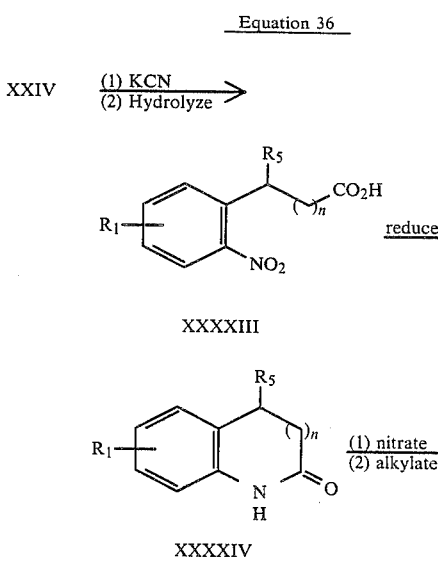

XXXXIII

XXXXIV

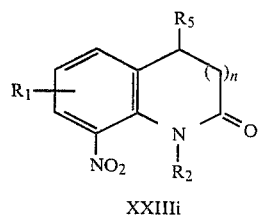

XXIIIi

The nitrobenzenes XXIV, previously discussed in Equation 21, are reacted with potassium cyanide in a solvent such as acetone to give nitrile intermediates which are hydrolized to the corresponding carboxylic acids XXXXIII by standard methods known to one skilled in the art. The nitro carboxylic acids XXXXIII, when reduced by standard methods (see discussion of Equation 20), spontaneously cyclize to give the lactams XXXXIV. For a discussion of this reaction when n is O, see W. Sumpter and F. Miller, *The Chemistry of Heterocyclic Compounds*, Vol. 8, Interscience Publishers, Inc., New York, 1954, p. 134–135, and references cited therein. For a discussion of this reaction when n is 1, see G. Jones, *The Chemistry of Heterocyclic Compounds*, Vol. 32, John Wiley and Sons, New York, 1977, p. 216–217, and references cited therein. The nitro lactams XXIIIi are prepared from lactams XXXXIV by the nitration, alkylation sequence described earlier for the preparation of nitro sultams XXIIIg in Equation 31.

Alternatively, many lactams XXXXIV of Equation 36 can be prepared from the substituted anilines XXXVII of Equation 32, as shown in Equation 37. $R_1$ and n are previously defined.

Equation 37

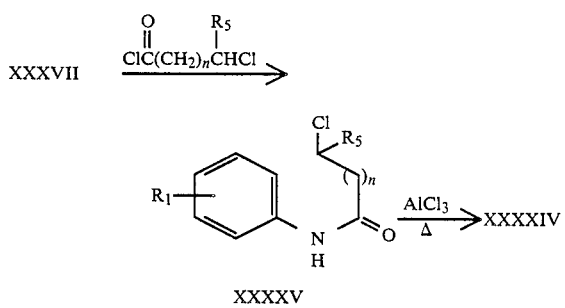

The substituted anilines XXXVII are reacted with either a chloroacetyl chloride (n=0) or β-chloropropionyl chloride (n=1, $R_5$=H) in the presence of an acid scavenger to give the chloro amides XXXXV. The amides XXXXV are cyclized by heating in the presence of a suitable Friedel-Crafts reagent such as $AlCl_3$ (see discussion of Equation 30) to give the lactams XXXXIV. The method of Equation 37 has been widely used for the preparation of oxindoles (XXXXIV, n=0; see W. Sumpter and F. Miller, loc. cit., p. 135-136 for discussion and references) and for the preparation of 3,4-dihydro-2-quinolones (XXXXIV, n=1; see G. Jones, loc. cit., p. 164-168 for discussion and references). For a general review of oxindole chemistry see W. Sumpter and F. Miller, loc. cit., p. 134-153.

As shown in Equation 38, many of the nitro compounds of Formula XXIII where J is $J_{10}$ (XXIIIj) can be prepared from the appropriately substituted phenols XXXX. R' is Br or $CH_2Cl$, $R_1$, $R_5$ and n are as previously defined.

Equation 38

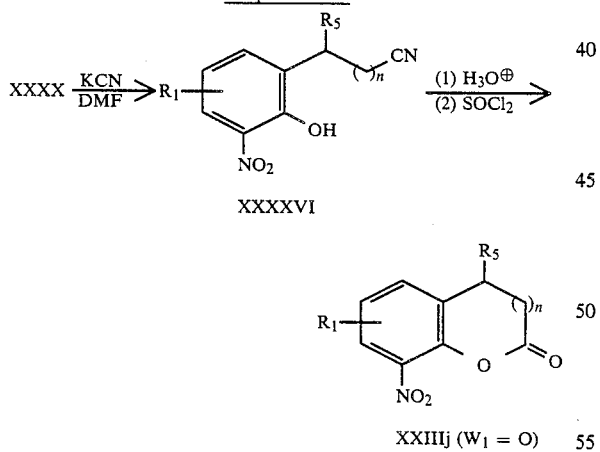

The nitrophenols XXXX, prepared by methods known to one skilled in the art, are reacted with potassium cyanide in a solvent such as DMF at 0° to 80° C. for 0.5 to 24 hours to give the cyanophenols XXXXVI. The cyano function is hydrolyzed to its corresponding carboxylic acid by methods known in the art. For n=0, the carboxylic acids cyclize spontaneously. For n=1, the carboxylic acid is cyclized by heating with a reagent such as thionyl chloride as taught by Wakselman et al. Tetrahedron, 30 4069 (1974) for the preparation of substituted dihydrocoumarins and 2-benzofuranones. The corresponding compounds $J_{10}$ where $W_1$=S can be prepared similarly starting with the appropriate thiophenol.

Alternatively, as shown in Equation 39, many of the nitro compounds of Formula XXIIIj where n=1 can be prepared by reducing the corresponding coumarins XXIIIp, which are readily prepared from nitrosalicaldehydes XXXXVII by heating with, for example where $R_3$ is H, potassium acetate in acetic anhydride according to the teachings of Gqola, et al., Fort. Hare Pap., 6, 197 (1975) (Chem. Abst. 84:150452X (1975)) for the preparation of 8-nitrocoumarin (XXIIIp, $R_1$=H). Coumarins are well known in the literature, for a review see Comprehensive Organic Chemistry, Vol. 4, Pergamon Press 1979.

Equation 39

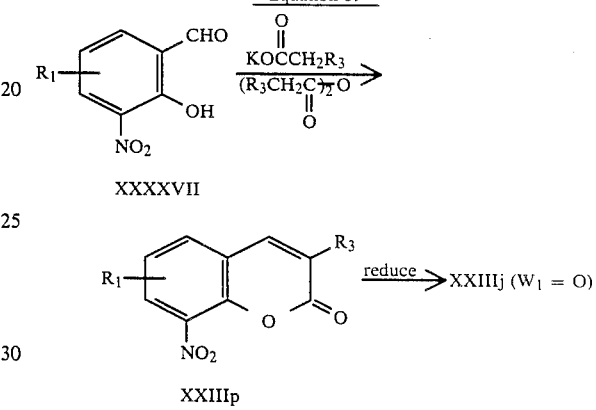

As shown in Equation 40, many of the nitro compounds of Formula XXIII where J is $J_{11}$ and n is 0 (XXIIIk) can be prepared from the appropriately substituted nitrosalicaldehydes XXXXVIII. $R_6$ and $R_7$ are H, $R_1$ is as previously defined.

Equation 40

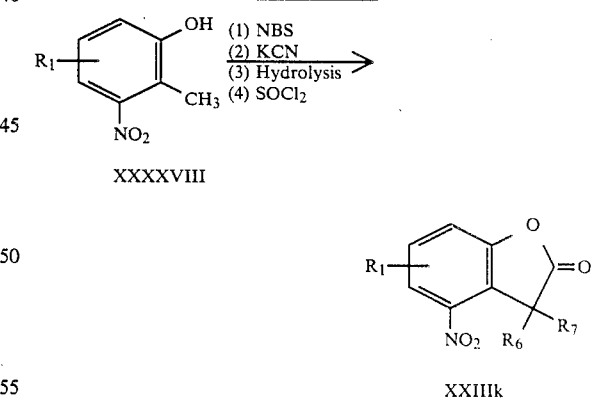

This method is parallel to that previously discussed for the preparation of Formula XXIIIj in Equation 38. The 2-benzofuranones XXIIIk, where $R_6$ and/or $R_7$ are other than hydrogen, can be prepared from the 2-benzofuranones XXIIIk where $R_6$ and/or $R_7$ are hydrogen by standard alkylation methods known in the art. For a review see: H. House, Modern Synthetic Reactions, 2nd Edition, W. A. Benjamin, Inc., Menlo Park, Calif. 1972, p. 542-570.

As shown in Equation 41, many of the nitro compounds of Formula XXIII where J is $J_{11}$ and n is 1 (XXIIIl) can be prepared from the appropriately substituted nitrophenylacetic acids IL. $R_1$, $R_6$ and $R_7$ are as previously defined.

Equation 41

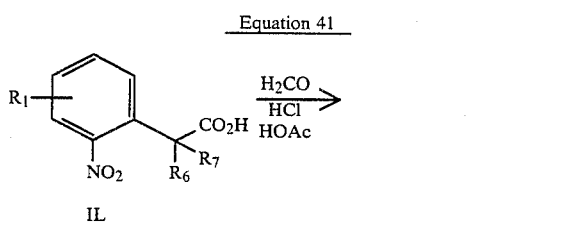

The nitrophenylacetic acids, prepared by methods known to one skilled in the art, are treated with formaldehyde in the presence of a strong acid such as HCl in a solvent such as solvent such as acetic acid at 25° to 100° C. for 2 to 48 hours. This method has been used to prepare substitutedbenzopyran-3-ones, see U.S. Pat. No. 3,480,634 (Chem. Abst. 72:43486s (1970)).

Alternatively, as shown in Equation 42, many benzo[c]pyran-3-ones XXIIIl can be prepared from the appropriately substituted nitrotoluic acids L. $R_6$ and $R_7$ are H, $R_1$ is as previously defined.

Equation 42

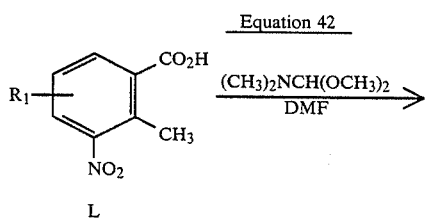

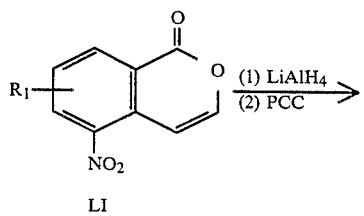

The nitrotoluic acids, prepared by methods known to one skilled in the art, are heated with dimethylformamide dimethylacetal in DMF to produce, in part, the nitroisocoumarins LI. The isocoumarins are reduced by lithium aluminum hydride to give a hemiacetal which is then separated and oxidized with pyridinium chlorochromate (PCC) to give the desired benzopyran-3-ones. This is the method taught by Somei and Shoda, *Heterocycles*, 17, 417 (1982) for the preparation of 1,4-dihydro-5-nitrobenzopyran-3-one (XXIIIl, $R_1$, $R_6$ and $R_7$=H).

The benzo[c]pyran-3-ones XXIIIl where $R_6$ and/or $R_7$ are other than hydrogen can be prepared by the standard alkylation methods discussed for Equation 40.

Additionally, many benzopyran-3-ones XXIIIl, where $R_1$ is other than $SCH_3$, can be prepared by the Baever-Villiger oxidation of 2-indanones XXIIIm (n=0) (vide infra). The Baeyer-Villiger oxidation of ketones to esters is well known in the literature, for a review see: *Organic Reactions*, Vol. 9, John Wiley and Sons, New York, 1957, p. 73 to 107. For application of this reaction to 2-indanones see G. Swan *J. Chem. Soc.*, 1720 (1949).

As shown in Equation 43, many of the nitro compounds of Formula XXIII, where J is $J_{12}$ (XXIIIm), can be prepared from the appropriately substituted indenes and dihydronaphthalenes of Formula LII. $R_7$ is H, $R_1$, $R_6$ and n are as previously defined.

Equation 43

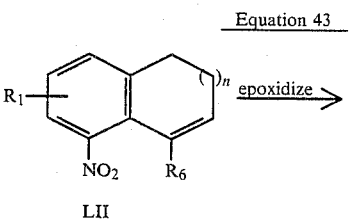

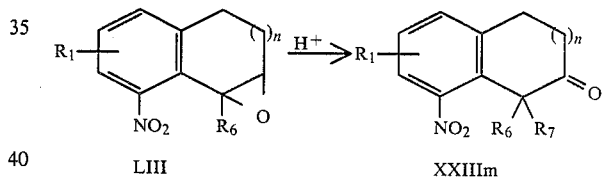

The nitroolefins LII can be converted to their corresponding epoxides LIII by either direct oxidation with a peracid such as m-chloroperbenzoic acid or via hydrobromination followed by treatment with a base as known to one skilled in the art. The epoxides LIII are rearranged to the desired 2-indanones (XXIIIm, n=0) or tetralones (XXIIIm, n=1) by reaction with either a protonic acid such as sulfuric acid as taught by Rosen et al., *J. Org. Chem.*, 29, 1723 (1964) or a Lewis Acid such as $BF_3$-etherate as taught by Bondinell and Pendleton, U.S. Pat. No. 4,192,888 (1980).

The starting nitroindenes (LII, n=0) and nitrodihydronaphthalenes (LII, n=1) are well known in the literature and can be prepared by methods known to one skilled in the art.

Alternatively, as shown in Equation 44, many of the 2-tetralones of Formula XXIIIm (n=1) can be prepared from the appropriately substituted nitrophenylacetic acids XXXXIX discussed previously in Equation 41 by reaction with ethylene under Friedel-Crafts conditions. For a review of this and alternate syntheses of 2-tetralones see Shner and Przhiyaglovskaya, *Russian Chemical Reviews*, 35, 523 (1966).

Equation 44

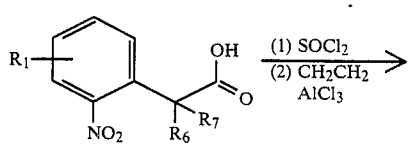

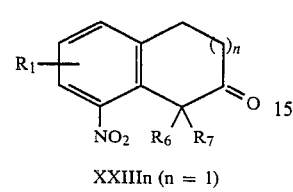

XXIIIn (n = 1)

Additionally, many of the 2-indanones (XXIIIm, n=0) and 2-tetralones (XXIIIm, n=1) can be prepared from the corresponding 1-indanones (XXIIIf, n=0) and 1-tetralones (XXIIIf, n=1), respectively, via a 1,2-carbonyl transposition, as shown in Equation 45. $R_1$, $R_6$ and n are as previously defined.

Equation 45

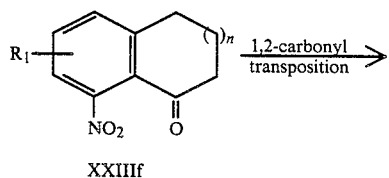

XXIIIf

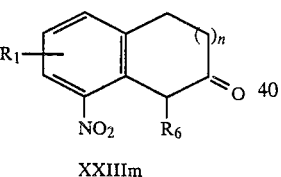

XXIIIm 1,2-Carbonyl transpositions are well known in the literature and can be performed by a wide variety of methods, for a recent review, see: D. G. Morris, *Chem. Soc. Reviews,* II, 397–434 (1983). For application of this method to indanones, see U.S. Pat. No. 4,192,888. For application of the method to tetralones, see Shner and Przhiyaglovskaya loc. cit.

As shown in Equation 46, many of the nitro compounds of Formula XXIII, where J is $J_{22}$ (XXIIIn), can be prepared from the appropriately substituted nitrophenols LIV. $R_1$, $R_3$, $R_4$ and n are as previously defined.

Equation 46

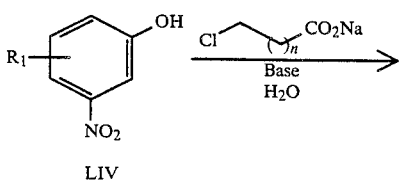

LIV

-continued
Equation 46

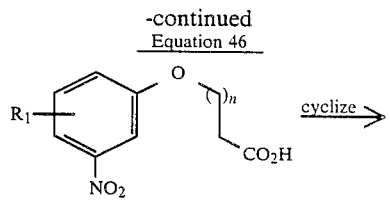

LV

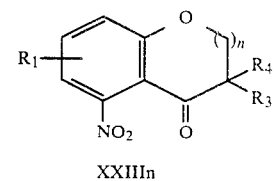

XXIIIn

The reaction of the nitrophenol LIV with the haloacid salts produces the nitro ethers LV which are subsequently cyclized, in part, to give XXIIIn ($R_3$, R=H) by heating the acid with a suitable condensing agent such as polyphosphoric acid, hydrofluoric acid, sulfuric acid or stannic chloride, or the acid may be converted to its chloride and heated with a typical Friedel-Crafts reagent such as aluminum chloride or stannic chloride. The ketones of Formula XXIIIn where $R_3$ and/or $R_4$ are other than hydrogen can be prepared from ketones XXIIIn where $R_3$ and/or $R_4$ are hydrogen by standard ketone alkylation and halogenation methods as described previously for compounds of Equation 30. The nitro compounds where $J=J_{22}$ and $W_1=S$ can be prepared analogously starting with the appropriate thiophenols.

Alternatively, as shown in Equation 47, many of the compounds of Formula XXIIIn where n=0 can be prepared from nitrobenzoates of Formula LVI. $R_1$, $R_3$ and $R_4$ are as previously defined.

Equation 47

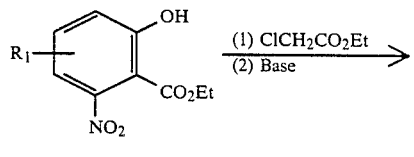

LVI

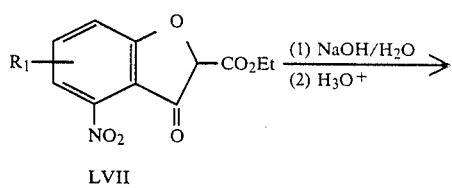

LVII

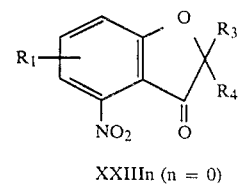

XXIIIn (n = 0)

The phenol LVI is first alkylated with ethyl chloroacetate in the presence of an acid scavenger followed by reaction with a base to effect cyclization to the ketoester LVII. The ketoester is then saponafied and decarboxylated by heating with acid to give the 3-ketobenzofurans XXIIIn (n=0). 3-Ketobenzofurans are well known in the art, for a review of their synthesis and chemistry see *Chemistry of Heterocyclic Compounds,* Vol. 29, Interscience Publishers, Inc., New York, 1974, p. 210–296.

Benzopyran-4-ones are also well known in the art, for a review see *Chemistry of Heterocyclic Compounds, Vol.* 31, Interscience Publishers, Inc., New York, 1977. For a review of the synthesis and chemistry of benzoxepin-5-ones see *Chemistry of Heterocyclic Compounds,* Vol. 26, Interscience Publishers, Inc., New York, 1972.

Many of the nitro compounds of Formula XXIII in Equation 20, where J is $J_{13}$, $J_{14}$, $J_{15}$, $J_{16}$, $J_{17}$, $J_{18}$, $J_{19}$, $J_{20}$, $J_{21}$ or $J_{23}$ can be prepared from the nitro compounds of Formula XXIII where J is $J_1$, $J_2$, $J_3$, $J_4$ ($J_{24}$), $J_5$, $J_7$, $J_8$, $J_9$, $J_{10}$ or $J_{22}$, respectively, (n=1) by the bromination/dehydrobromination sequence described above for sulfonamides IV in Equation 11.

Alternately, nitro compounds of Formula XXIII in Equation 20 where J is $J_{15}$ can be prepared from nitro compounds of Formula XXIII where J is $J_{16}$ by treatment with the appropriate amines $R_2NH_2$ as taught by J. Jones and A. Pinder, *J. Chem. Soc.,* 2612 (1958). Additionally, the nitro compounds of Formula XXIII where J is $J_{21}$ can be prepared as discussed in Equation 39.

Many of the nitro compounds of Formula XXIII in Equation 20 where J is $J_{18}$ can also be prepared from ketones XXXIX by base treatment of its tosylhydrazone derivative as taught by B. Loev, et al., *J. Org. Chem.,* 31, 3531 (1966).

The preparation of compounds of Formula I where J is $J_1$ to $J_{12}$ and $J_{22}$ and n=2 can be prepared using the procedures outlined above for the analogous compounds where n=1.

The amines of Formula III in Equations 1 and 3 are also important intermediates for the preparation of the compounds of this invention. The amines can be prepared by the methods taught in South African Patent Application No. 837,434 or by suitable modifications thereof as known to one skilled in the art.

2-Aminopyrimidines and 2-aminotriazines are well known in the art. For a review of the synthesis and reactions of 2-aminopyrimidines see *The Chemistry of Heterocyclic Compounds,* Vol. 16, John Wiley and Sons, New York (1962). For a review of the synthesis and reactions of 2-amino-s-triazines see *The Chemistry of Heterocyclic Compounds,* Vol. 13, John Wiley, New York (1959), F. C. Schaefer, U.S. Pat. No. 3,154,547 and F. C. Schaefer and K. R. Huffman, *J. Org. Chem.,* 28, 1812 (1963).

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate, or hydride). Quaternary amine salts can be made by similar techniques.

Salts of compounds of Formula I can also be prepared by exchange of one cation for another. Cationic exchange can be effected by direct contacting of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

EXAMPLE 1

2-t-Butyl-3-hydroxy-7-chloro-2,3-dihydro-1,2-benzisothiazole-1,1-dioxide

To a solution of 49.5 g of N-t-butyl-2-chlorobenzenesulfonamide in 875 mls of dry THF was added 262 ml of a 1.6M hexane solution of n-butyl lithium at −20° to −5° C. under an inert atmosphere. The mixture was stirred at 0° C. for 1 hour, room temperature for 2 hours, recooled to −78° C. and contacted with 38 mls of dry dimethylformamide. The mixture was allowed to warm to room temperature overnight, poured into water, acidified to a ph of ~3 and ether extracted. The extract was washed with water and brine, dried over $MgSO_4$ and concentrated to give a yellow oil. The oil was dissolved in 50% ether in hexane solution and allowed to stand, giving, after filtration, 38 g of the title compound as colorless crystals, m.p. 139°–141° C.

90 MHz NMR ($CDCl_3$) δ: 7.7–7.2 (m, 3H, arom); 5.9 (br, d, J=11 Hz, 1H, CH or OH); 4.2 (br, d, J=11 Hz, 1H, OH or CH); and 1.5 (s, 9H, $CH_3$'s).

IR (nujol) 3440 $cm^{-1}$.

EXAMPLE 2

7-Chloro-1,2-benzisothiazole-1,1-dioxide

A solution of 37 g of 2-t-butyl-3-hydroxy-7-chloro-2,3-dihydro-1,2-benzisothiazole-1,1-dioxide and 0.2 g of tosic acid in 370 mls of benzene was refluxed through a Dean-Stark water separator for 16 hours, cooled in ice and filtered to give 18.9 g of the title compound as colorless crystals, m.p. 162°–164° C.

90 MHz NMR ($CDCl_3$) δ: 9.15 (s, 1H, CH); and 8.0–7.7 (m, 3H, arom).

IR (nujol) 1445, 1320, 1170 $cm^{-1}$.

EXAMPLE 3

7-Chloro-2,3-dihydro-1,2-benzisothiazole-1,1-dioxide

A suspension of 17.9 g of 7-chloro-1,2-benzisothiazole-1,1-dioxide in 180 ml of absolute ethanol was cooled to 0° C. and treated with 3.33 g of sodium borohydride at such a rate that the temperature remained below 5° C. The mixture was warmed to room temperature for 30 minutes, recooled to 0° C. and treated with glacial acetic acid to destroy excess hydride. The mixture was concentrated to dryness, the resulting solid suspended in water, filtered, washed with water and dried in vacuo at 50° C. for 16 hours to give 17.6 g of the title compound as a white powder, m.p. 159°–161° C.

90 MHz NMR ($CDCl_3/DMSO-d_6$) δ: 7.9–7.2 (m, 3H, arom); 6.9 (br, 1H, NH); and 4.4 (s, 2H, $CH_2$).

IR (nujol) 3220 $cm^{-1}$.

EXAMPLE 4

2-Methyl-7-chloro-2,3-dihydro-1,2-benzisothiazole-1,1-dioxide

A solution of 16.6 g of 7-chloro-2,3-dihydro-1,2-benzisothiazole-1,1-dioxide in 85 mls of dry dimethylformamide was cooled and treated with 10 g of potassium t-butoxide at such a rate that the temperature remained below 6° C. The resulting suspension was stirred at 5° to 10° C. for 30 minutes, treated with 6.1 mls of methyl iodide at 10° to 15° C. and stirred at room temperature for 16 hours. The mixture was poured into ice water and the resulting solid was filtered, washed with water and dried in vacuo at 50° C. for 1.5 hours to give 15.4 g of the title compound as a pinkish solid, m.p. 95°–97° C.

90 MHz NMR (CDCl$_3$) δ: 7.8–7.2 (m, 3H, arom); 4.4 (s, 2H, CH$_2$); and 3.0 (s, 3H, CH$_3$).

IR (nujol) 1460, 1300, 1165, 1152 cm$^{-1}$.

EXAMPLE 5

2-Methyl-7-(phenylmethylthio)-2,3-dihydro-1,2-benzisothiazole-1,1-dioxide

To a solution of 12 g of potassium-t-butoxide in 100 ml of dry dimethylformamide was added 12.9 mls of benzyl mercaptan at −5° to 0° C. under an inert atmosphere followed by 12.2 g of 2-methyl-7-chloro-2,3-dihydro-1,2-benzisothiazole-1,1-dioxide. The mixture was stirred at room temperature for 16 hours and poured into water to give a gummy solid. The water was decanted and extracted with ethyl acetate. The gummy solid was slurried in ethyl acetate and filtered to give 5.9 g of the title compound as a light orange solid, m.p. 119°–112° C. The combined ethyl acetate extract and filtrate were washed with water and brine, dried over MgSO$_4$ and concentrated to a solid which was slurried in ether and filtered to give an additional 7.6 g of product, m.p. 121°–124° C. Total yield was 13.5 g.

90 MHz NMR (CDCl$_3$) δ: 7.5–7.3 (m, 8H arom); 4.3 (br, s, 4H, CH$_2$'s); and 2.9 (s, 3H, CH$_3$).

IR (nujol) 1455, 1290, 1155 cm$^{-1}$.

EXAMPLE 6

2-Methyl-2,3-dihydro-1,2-benzisothiazole-7-sulfonamide-1,1-dioxide

To a solution of 9.8 g of 2-methyl-7-(phenylmethylthio)-2,3-dihydro-1,2-benzisothiazole-1,1-dioxide and 1.44 mls of water in 200 mls of 1,2-dichloroethane was added a solution of 12.9 mls of sulfuryl chloride in 50 mls of 1,2-dichloroethane, dropwise, at 65° to 70° C. The mixture was heated at 70° to 75° C. for 2 hours, cooled to room temperature and concentrated. The residue was dissolved in 100 ml of methylene chloride and added to a solution of 4.0 ml of liquified ammonia in 200 mls of methylene chloride at −78° to −40° C. The mixture was warmed to room temperature, stirred for 16 hours, concentrated and the resulting white solid was suspended in 150 mls of 1N HCl, filtered, washed with water and ether and dried in vacuo at 70° C. to 5.0 g of the title compound as a white powder, m.p. 195°–197° C. (a similar preparation had m.p. 203°–205° C.).

90 MHz NMR (CDCl$_3$/DMSO) δ: 8.2–7.7 (m, 3H, arom); 7.5 (b, 2H NH$_2$); 4.4 (s, 2H, CH$_2$); and 2.9 (s, 3H, CH$_3$).

IR (nujol) 3330, 3230 cm$^{-1}$.

EXAMPLE 7

N-(Butylaminocarbonyl)-2-methyl-2,3-dihydro-1,2-benzisothiazole-7-sulfonamide-1,1-dioxide A suspension of 13.0 g of 2-methyl-2,3-dihydro-1,2-benzisothiazole-7-sulfonamide-1,1-dioxide, 11.2 ml of butyl isocyanate and 13.8 g of potassium carbonate in 200 ml of dry methyl ethyl ketone was heated at reflux for 2 hours. 13.8 g of potassium carbonate was added and heating was continued for an additional 16 hours. The mixture was cooled, the solvent was decanted from the solids, concentrated in vacuo, the residue dissolved in ethyl acetate and washed with saturated aq. NaHCO$_3$. The aqueous wash was added to the original solids diluted with water and acidified to pH 3 with dilute HCl. The mixture was extracted with methylene chloride, the extract was washed with water and brine, dried and concentrated in vacuo leaving a solid which was slurried in ether and filtered to give 13.24 g of the title compound as a white powder, m.p. 162°–164° C.

90 MHz NMR (CDCl$_3$) δ: 8.4–7.5 (m, 3H, arom); 6.4 (b, t, 1H, NH); 5.8 (b, 1H, NH); 4.4 (s, 2H, CH$_2$); 3.1 (m, 2H, CH$_2$); 3.0 (s, 3H, CH$_3$); and 1.7–0.7 (m, 7H, alkyl).

IR (nujol) 3350, 3240, 1680 cm$^{-1}$.

EXAMPLE 8

2-Methyl-2,3-dihydro-1,2-benzisothiazole-7-sulfonylisocyanate, 1,1-dioxide

A mixture of 13.2 g N-(butylaminocarbonyl)-2-methyl-2,3-dihydro-1,2-benzisothiazole-7-sulfonamide-1,1-dioxide, 3.7 ml of butyl isocyanate and 0.1 g of DABCO was treated with 3.5 ml of phosgene at 135°–138° C. for 2 hours, purged with N$_2$ and cooled to 0° C. depositing a solid which was filtered under nitrogen to give 5.5 g of 2-methyl-2,3-dihydro-1,2-benzisothiazole-7-sulfonylisocyanate-1,1-dioxide as a cream colored solid, m.p. 176°–180° C., IR (nujol) 2220 cm$^{-1}$.

EXAMPLE 9

N-[(4-Cyclopropyl-6-methoxy-1,3,5-triazin-2-yl)aminocarbonyl]-2-methyl-2,3-dihydro-1,2-benzisothiazole-7-sulfonamide, 1,1-dioxide To a solution of 0.69 g (2.0 mmol) of 2-methyl-2,3-dihydro-1,2-benzisothiazole-7-sulfonylisocyanate, 1,1-dioxide in 10 ml of dry methylene chloride is added 1.0 mmol of 2-amino-4-methoxy-6-cyclopropyltriazine. The mixture is heated to reflux for 5 minutes and stirred at 25° C. for 1 to 2 hours. The resulting solid is filtered, washed with methylene chloride and ether to give the title compound.

Using the procedures of Examples 1 to 9, the following compounds can be prepared.

TABLE I

| W | n | R | R₁ | R₂ | R₅ | Y | Z | m.p. (°C.) |
|---|---|---|---|---|---|---|---|---|
| O | 0 | H | H | CH₃ | H | CH₃ | CH | |
| O | 0 | H | H | CH₃ | H | CH₂CH₃ | CH | |
| O | 0 | H | H | CH₃ | H | OCH₃ | CH | |
| O | 0 | H | H | CH₃ | H | OCH₂CH₃ | CH | |
| O | 0 | H | H | CH₃ | H | CH₂OCH₃ | CH | |
| O | 0 | H | H | CH₃ | H | OCF₂H | CH | |
| O | 0 | H | H | CH₃ | H | SCF₂H | CH | |
| O | 0 | H | H | CH₃ | H | OCH₂CF₃ | CH | |
| O | 0 | H | H | CH₃ | H | CF₃ | CH | |
| O | 0 | H | H | CH₃ | H | OCH₂CH=CH₂ | CH | |
| O | 0 | H | H | CH₃ | H | OCH₂C≡CH | CH | |
| O | 0 | H | H | CH₃ | H | NHCH₃ | CH | |
| O | 0 | H | H | CH₃ | H | N(CH₃)₂ | CH | |
| O | 0 | H | H | CH₃ | H | CH(OCH₃)₂ | CH | |
| O | 0 | H | H | CH₃ | H | CH₃ | N | |
| O | 0 | H | H | CH₃ | H | CH₂CH₃ | N | |
| O | 0 | H | H | CH₃ | H | OCH₃ | N | |
| O | 0 | H | H | CH₃ | H | OCH₂CH₃ | N | |
| O | 0 | H | H | CH₃ | H | CH₂OCH₃ | N | |
| O | 0 | H | H | CH₃ | H | OCF₂H | N | |
| O | 0 | H | H | CH₃ | H | SCF₂H | N | |
| O | 0 | H | H | CH₃ | H | OCH₂CF₃ | N | |
| O | 0 | H | H | CH₃ | H | CF₃ | N | |
| O | 0 | H | H | CH₃ | H | OCH₂CH=CH₂ | N | |
| O | 0 | H | H | CH₃ | H | OCH₂C≡CH | N | |
| O | 0 | H | H | CH₃ | H | NHCH₃ | N | |
| O | 0 | H | H | CH₃ | H | N(CH₃)₂ | N | |
| O | 0 | H | H | CH₃ | H | CH(OCH₃)₂ | N | |
| O | 0 | H | H | CH₂CH₃ | H | OCH₃ | N | 152–166 |
| O | 0 | H | H | CH₂CH₂CH₃ | H | OCH₃ | N | |
| O | 0 | H | H | CH(CH₃)₂ | H | OCH₃ | N | |
| O | 0 | H | H | CH₂CH₂CH₂CH₃ | H | OCH₃ | N | |
| O | 0 | H | H | CH₂CH(CH₃)₂ | H | OCH₃ | N | 138–144 |
| O | 0 | H | H | CH(CH₃)CH₂CH₃ | H | OCH₃ | N | |
| O | 0 | H | H | C(CH₃)₃ | H | OCH₃ | N | |
| O | 0 | H | H | H | H | OCH₃ | N | 171–180 |
| O | 0 | H | H | CH₃ | CH₃ | OCH₃ | N | |
| O | 0 | CH₃ | H | CH₃ | H | OCH₃ | N | |
| S | 0 | H | H | CH₃ | H | OCH₃ | N | |
| O | 1 | H | H | CH₃ | H | OCH₃ | N | |
| O | 1 | H | H | CH₂CH₃ | H | OCH₃ | N | |
| O | 1 | H | H | CH₂CH₂CH₃ | H | OCH₃ | N | |
| O | 1 | H | H | CH(CH₃)₂ | H | OCH₃ | N | |
| O | 1 | H | H | CH₂CH₂CH₂CH₃ | H | OCH₃ | N | |
| O | 1 | H | H | CH₂CH(CH₃)₂ | H | OCH₃ | N | |
| O | 1 | H | H | CH(CH₃)CH₂CH₃ | H | OCH₃ | N | |
| O | 1 | H | H | C(CH₃)₃ | H | OCH₃ | N | |
| O | 1 | H | H | H | H | OCH₃ | N | |
| O | 0 | H | o-F | CH₃ | H | OCH₃ | N | |
| O | 0 | H | m-F | CH₃ | H | OCH₃ | N | |
| O | 0 | H | o-Cl | CH₃ | H | OCH₃ | N | |
| O | 0 | H | m-Cl | CH₃ | H | OCH₃ | N | 163–167(d) |
| O | 0 | H | o-Br | CH₃ | H | OCH₃ | N | |
| O | 0 | H | m-Br | CH₃ | H | OCH₃ | N | |
| O | 0 | H | o-CH₃ | CH₃ | H | OCH₃ | N | |
| O | 0 | H | m-CH₃ | CH₃ | H | OCH₃ | N | |
| O | 0 | H | o-OCH₃ | CH₃ | H | OCH₃ | N | |
| O | 0 | H | m-OCH₃ | CH₃ | H | OCH₃ | N | |
| O | 0 | H | o-CF₃ | CH₃ | H | OCH₃ | N | |
| O | 0 | H | m-CF₃ | CH₃ | H | OCH₃ | N | |
| O | 0 | H | o-SCH₃ | CH₃ | H | OCH₃ | N | |
| O | 0 | H | m-SCH₃ | CH₃ | H | OCH₃ | N | |
| O | 0 | H | o-OCF₂H | CH₃ | H | OCH₃ | N | |
| O | 0 | H | m-OCF₂H | CH₃ | H | OCH₃ | N | |
| O | 0 | H | p-F | CH₃ | H | OCH₃ | N | |
| O | 0 | H | p-Cl | CH₃ | H | OCH₃ | N | |
| O | 2 | H | H | CH₃ | H | OCH₃ | N | |

TABLE II

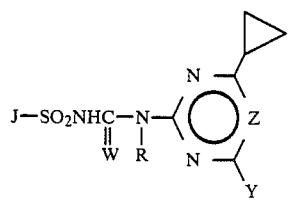

| J | W | n | $W_1$ | R | $R_1$ | $R_2$ | $R_5$ | $R_6$ | $R_7$ | Y | Z | m.p. (°C.) |
|---|---|---|---|---|---|---|---|---|---|---|---|---|
| J-2 | O | 0 | — | H | H | — | H | — | — | $OCH_3$ | N | |
| J-2 | O | 1 | — | H | H | — | H | — | — | $OCH_3$ | N | |
| J-3 | O | 0 | — | H | H | $CH_3$ | H | — | — | $OCH_3$ | N | |
| J-3 | O | 1 | — | H | H | $CH_3$ | H | — | — | $OCH_3$ | N | |
| J-4 | O | 0 | — | H | H | — | H | — | — | $OCH_3$ | N | 159–164 |
| J-4 | O | 0 | — | H | o-Cl | — | H | — | — | $OCH_3$ | N | |
| J-4 | O | 0 | — | H | m-Cl | — | H | — | — | $OCH_3$ | N | |
| J-4 | O | 0 | — | H | p-Cl | — | H | — | — | $OCH_3$ | N | |
| J-4 | O | 0 | — | H | m-$CH_3$ | — | H | — | — | $OCH_3$ | N | |
| J-4 | O | 0 | — | H | o-$OCH_3$ | — | H | — | — | $OCH_3$ | N | |
| J-4 | O | 1 | — | H | H | — | H | — | — | $OCH_3$ | N | |
| J-4 | O | 1 | — | H | o-Cl | — | H | — | — | $OCH_3$ | N | |
| J-4 | O | 1 | — | H | m-Cl | — | H | — | — | $OCH_3$ | N | |
| J-4 | O | 1 | — | H | p-Cl | — | H | — | — | $OCH_3$ | N | |
| J-4 | O | 1 | — | H | m-$CH_3$ | — | H | — | — | $OCH_3$ | N | |
| J-4 | O | 1 | — | H | o-$OCH_3$ | — | H | — | — | $OCH_3$ | N | |
| J-5 | O | 0 | — | H | H | — | H | — | — | $OCH_3$ | N | |
| J-5 | O | 1 | — | H | H | — | H | — | — | $OCH_3$ | N | |
| J-7 | O | 0 | — | H | H | $CH_3$ | H | — | — | $OCH_3$ | N | |
| J-7 | O | 1 | — | H | H | $CH_3$ | H | — | — | $OCH_3$ | N | |
| J-8 | O | 0 | — | H | H | — | H | — | — | $OCH_3$ | N | |
| J-8 | O | 1 | — | H | H | — | H | — | — | $OCH_3$ | N | |
| J-9 | O | 0 | — | H | H | $CH_3$ | H | — | — | $OCH_3$ | N | |
| J-9 | O | 1 | — | H | H | $CH_3$ | H | — | — | $OCH_3$ | N | |
| J-8 | O | 1 | — | H | m-Br | — | H | — | — | $OCH_3$ | N | 174–179 |
| J-10 | O | 0 | O | H | H | — | H | — | — | $OCH_3$ | N | |
| J-10 | O | 0 | S | H | H | — | H | — | — | $OCH_3$ | N | |
| J-10 | O | 1 | O | H | H | — | H | — | — | $OCH_3$ | N | |
| J-10 | O | 1 | S | H | H | — | H | — | — | $OCH_3$ | N | |
| J-11 | O | 0 | O | H | H | — | H | — | — | $OCH_3$ | N | |
| J-11 | O | 0 | O | H | H | — | H | $CH_3$ | — | $OCH_3$ | N | |
| J-11 | O | 0 | O | H | H | — | H | $CH_3$ | $CH_3$ | $OCH_3$ | N | |
| J-11 | O | 0 | S | H | H | — | H | H | H | $OCH_3$ | N | |
| J-11 | O | 1 | O | H | H | — | H | H | H | $OCH_3$ | N | |
| J-11 | O | 1 | S | H | H | — | H | H | H | $OCH_3$ | N | |
| J-12 | O | 0 | O | H | H | — | H | H | H | $OCH_3$ | N | |
| J-12 | O | 1 | O | H | H | — | H | H | H | $OCH_3$ | N | |
| J-13 | O | — | — | H | H | $CH_3$ | — | — | — | $OCH_3$ | N | |
| J-14 | O | — | — | H | H | — | — | — | — | $OCH_3$ | N | |
| J-15 | O | — | — | H | H | $CH_3$ | — | — | — | $OCH_3$ | N | |
| J-17 | O | — | — | H | H | — | — | — | — | $OCH_3$ | N | |
| J-18 | O | — | — | H | H | $CH_3$ | — | — | — | $OCH_3$ | N | |
| J-19 | O | — | — | H | H | — | — | — | — | $OCH_3$ | N | |
| J-20 | O | — | — | H | H | $CH_3$ | — | — | — | $OCH_3$ | N | |
| J-25 | O | — | O | H | H | — | — | H | H | $OCH_3$ | N | |
| J-25 | O | — | S | H | H | — | — | H | H | $OCH_3$ | N | |
| J-26 | O | — | — | H | H | $CH_3$ | — | H | H | $OCH_3$ | N | |
| J-26 | O | — | — | H | H | $CH_3$ | — | H | H | $OCH_3$ | N | |
| J-4 | O | 0 | — | H | H | — | H | — | — | $OCH_3$ | CH | |
| J-4 | O | 0 | — | H | H | — | H | — | — | $CH_3$ | CH | |
| J-4 | O | 0 | — | H | H | — | H | — | — | $OCH_2CH_3$ | N | |
| J-4 | O | 1 | — | H | H | — | H | — | — | $OCH_3$ | CH | |
| J-4 | O | 1 | — | H | H | — | H | — | — | $CH_3$ | CH | |
| J-4 | O | 1 | — | H | H | — | H | — | — | $OCH_2CH_3$ | N | |

TABLE III

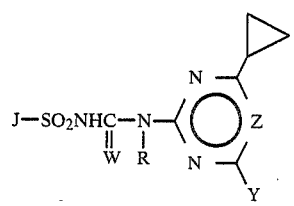

| J | W | n | W₁ | R | R₁ | R₃ | R₄ | R₅ | Y | Z | m.p. (°C.) |
|---|---|---|---|---|---|---|---|---|---|---|---|
| J-6 | O | 0 | — | H | H | H | H | H | OCH₃ | N | |
| J-6 | O | 0 | — | H | H | CH₃ | H | H | OCH₃ | N | |
| J-6 | O | 0 | — | H | H | CH₂CH₃ | H | H | OCH₃ | N | |
| J-6 | O | 0 | — | H | H | CH₂CH₂CH₃ | H | H | OCH₃ | N | |
| J-6 | O | 0 | — | H | H | CH(CH₃)₂ | H | H | OCH₃ | N | |
| J-6 | O | 0 | — | H | H | CH₂CH₂CH₂CH₃ | H | H | OCH₃ | N | |
| J-6 | O | 0 | — | H | H | CH₂CH(CH₃)₂ | H | H | OCH₃ | N | |
| J-6 | O | 0 | — | H | H | CH(CH₃)CH₂CH₃ | H | H | OCH₃ | N | |
| J-6 | O | 0 | — | H | H | Cl | H | H | OCH₃ | N | |
| J-6 | O | 0 | — | H | H | Cl | Cl | H | OCH₃ | N | |
| J-6 | O | 0 | — | H | H | Br | Br | H | OCH₃ | N | |
| J-6 | O | 1 | — | H | H | H | H | H | OCH₃ | N | |
| J-6 | O | 0 | — | H | H | CH₃ | CH₃ | H | OCH₃ | N | |
| J-16 | O | — | — | H | H | — | H | — | OCH₃ | N | |
| J-16 | O | — | — | H | H | — | CH₃ | — | OCH₃ | N | |
| J-16 | O | — | — | H | H | — | CH₂CH₃ | — | OCH₃ | N | |
| J-16 | O | — | — | H | H | — | CH₂CH₂CH₃ | — | OCH₃ | N | |
| J-16 | O | — | — | H | H | — | CH₂CH₂CH₂CH₃ | — | OCH₃ | N | |
| J-16 | O | — | — | H | m-Cl | — | H | — | OCH₃ | N | |
| J-16 | O | — | — | H | o-Cl | — | H | — | OCH₃ | N | |
| J-16 | O | — | — | H | p-Cl | — | H | — | OCH₃ | N | |
| J-21 | O | — | — | H | H | H | — | — | OCH₃ | N | |
| J-21 | O | — | — | H | H | CH₃ | — | — | OCH₃ | N | |
| J-22 | O | 0 | O | H | H | H | H | — | OCH₃ | N | |
| J-22 | O | 0 | S | H | H | H | H | — | OCH₃ | N | |
| J-22 | O | 1 | O | H | H | H | H | — | OCH₃ | N | |
| J-23 | O | — | — | H | H | H | — | — | OCH₃ | N | |
| J-24 | O | — | — | H | H | — | CH₃ | CH₃ | OCH₃ | N | |
| J-24 | O | — | — | H | H | — | CH₃ | H | OCH₃ | N | 182–185 |
| J-24 | O | — | — | H | H | — | CH₂CH₃ | H | OCH₃ | N | |
| J-24 | O | — | — | H | H | — | CH₂CH₂CH₃ | H | OCH₃ | N | |
| J-24 | O | — | — | H | H | — | CH(CH₃)₂ | H | OCH₃ | N | |
| J-24 | O | — | — | H | H | — | CH₂CH₂CH₂CH₃ | H | OCH₃ | N | |
| J-24 | O | — | — | H | H | — | CH₂CH(CH₃)₂ | H | OCH₃ | N | |
| J-24 | O | — | — | H | H | — | CH(CH₃)CH₂CH₃ | H | OCH₃ | N | |
| J-24 | O | — | — | H | H | — | C(CH₃)₃ | H | OCH₃ | N | |
| J-24 | O | — | — | H | H | — | Cl | H | OCH₃ | N | |
| J-24 | O | — | — | H | H | — | Br | H | OCH₃ | N | |
| J-24 | O | — | — | H | o-Cl | — | CH₃ | H | OCH₃ | N | |
| J-24 | O | — | — | H | m-Cl | — | CH₃ | H | OCH₃ | N | |
| J-24 | O | — | — | H | p-Cl | — | CH₃ | H | OCH₃ | N | |
| J-24 | O | — | — | H | m-CH₃ | — | CH₃ | H | OCH₃ | N | |
| J-24 | O | — | — | H | m-OCH₃ | — | CH₃ | H | OCH₃ | N | |
| J-16 | O | — | — | H | H | — | H | — | OCH₃ | CH | |
| J-16 | O | — | — | H | H | — | H | — | CH₃ | CH | |
| J-16 | O | — | — | H | H | — | H | — | OCH₂CH₃ | N | |
| J-24 | O | 1 | — | H | H | — | CH₃ | H | OCH₃ | CH | |
| J-24 | O | 1 | — | H | H | — | CH₃ | H | CH₃ | CH | |
| J-24 | O | 1 | — | H | H | — | CH₃ | H | OCH₂CH₃ | N | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE IV

| | Active Ingredient | Weight Percent* | |
|---|---|---|---|
| | | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength | 90–99 | 0–10 | 0–2 |

TABLE IV-continued

|  | Weight Percent* | |
|---|---|---|
| Active Ingredient | Diluent(s) | Surfactant(s) |
| Compositions | | |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 10

| Wettable Powder | |
|---|---|
| N—[(4-cyclopropyl-6-methoxy-1,3,5-triazin-2-yl)-aminocarbonyl]-2,3-dihydro-2-methyl-1,2-benzisothiazole-7-sulfonamide, 1,1-dioxide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 11

| Wettable Powder | |
|---|---|
| N—[(4-cyclopropyl-6-methoxy-1,3,5-triazin-2-yl)-aminocarbonyl]-2,3-dihydro-2-methyl-1,2-benzisothiazole-7-sulfonamide, 1,1-dioxide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 12

| Granule | |
|---|---|
| Wettable Powder of Example 11 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE 13

| Extruded Pellet | |
|---|---|
| N—[(4-cyclopropyl-6-methoxy-1,3,5-triazin-2-yl)-aminocarbonyl]-2,3-dihydro-2-methyl-1,2-benzisothiazole-7-sulfonamide, 1,1-dioxide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 14

| Oil Suspension | |
|---|---|
| N—[(4-cyclopropyl-6-methoxy-1,3,5-triazin-2-yl)-aminocarbonyl]-2,3-dihydro-2-methyl-1,2-benziso- | 25% |

-continued

| Oil Suspension | |
|---|---|
| thiazole-7-sulfonamide, 1,1-dioxide | |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 15

| Wettable Powder | |
|---|---|
| N—[(4-cyclopropyl-6-methoxy-1,3,5-triazin-2-yl)-aminocarbonyl]-2,3-dihydro-2-methyl-1,2-benzisothiazole-7-sulfonamide, 1,1-dioxide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 16

| Low Strength Granule | |
|---|---|
| N—[(4-cyclopropyl-6-methoxy-1,3,5-triazin-2-yl)-aminocarbonyl]-2,3-dihydro-2-methyl-1,2-benzisothiazole-7-sulfonamide, 1,1-dioxide | 1% |
| N,N—dimethylformamide | 9% |
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 17

| Aqueous Suspension | |
|---|---|
| N—[(4-cyclopropyl-6-methoxy-1,3,5-triazin-2-yl)-aminocarbonyl]-2,3-dihydro-2-methyl-1,2-benzisothiazole-7-sulfonamide, 1,1-dioxide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 18

| Solution | |
|---|---|
| N—[(4-cyclopropyl-6-methoxy-1,3,5-triazin-2-yl)aminocarbonyl]-2,3-dihydro-2-methyl-1,2-benzisothiazole-7-sulfonamide, 1,1-dioxide, sodium salt | 5% |
| water | 95% |

The salt is added directly to the water with stirring to produce the solution, which may then be packaged for use.

EXAMPLE 19

| Low Strength Granule | |
|---|---|
| N—[(4-cyclopropyl-6-methoxy-1,3,5-triazin-2-yl)-aminocarbonyl]-2,3-dihydro-2-methyl-1,2-benzisothiazole-7-sulfonamide, 1,1-dioxide | 0.1% |
| attapulgite granules (U.S.S. 20-40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 20

| Granule | |
|---|---|
| N—[(4-cyclopropyl-6-methoxy-1,3,5-triazin-2-yl)-aminocarbonyl]-2,3-dihydro-2-methyl-1,2-benzisothiazole-7-sulfonamide, 1,1-dioxide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 21

| High Strength Concentrate | |
|---|---|
| N—[(4-cyclopropyl-6-methoxy-1,3,5-triazin-2-yl)-aminocarbonyl]-2,3-dihydro-2-methyl-1,2-benzisothiazole-7-sulfonamide, 1,1-dioxide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 22

| Wettable Powder | |
|---|---|
| N—[(4-cyclopropyl-6-methoxy-1,3,5-triazin-2-yl)- | 90% |

| -continued | |
|---|---|
| Wettable Powder | |
| aminocarbonyl]-2,3-dihydro-2-methyl-1,2-benziso- thiazole-7-sulfonamide, 1,1-dioxide | |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 23

| Wettable Powder | |
|---|---|
| N—[(4-cyclopropyl-6-methoxy-1,3,5-triazin-2-yl)-aminocarbonyl]-2,3-dihydro-2-methyl-1,2-benzisothiazole-7-sulfonamide, 1,1-dioxide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 24

| Oil Suspension | |
|---|---|
| N—[(4-cyclopropyl-6-methoxy-1,3,5-triazin-2-yl)-aminocarbonyl]-2,3-dihydro-2-methyl-1,2-benzisothiazole-7-sulfonamide, 1,1-dioxide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

Utility

The compounds of the present invention are active herbicides. They should have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures, or on fallow land.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.001 to 5 kg/ha, the lower rates being suggested for use on lighter soils and/or those having a low organic matter content, for selective weed control or for situations where only short-term persistence is required.

The compounds of the invention may be used in combination with any other commercial herbicide; examples of which are those of the triazine, triazole, uracil, urea, amide, diphenylether, carbamate and bipyridylium types.

The herbicidal properties of the subject compounds were observed in greenhouse tests. The test procedures follow.

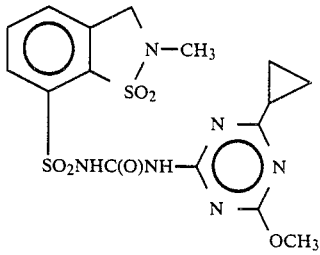

Compound 1

Test A

Seeds of crabgrass (Digitaria sp.), barnyardgrass (Echinochloa crusgalli), wild oats (Avena fatua), cheatgrass (Bromus secalinus), velvetleaf (Abutilon theophrasti), morningglory (Ipomoea sp.), cocklebur (Xanthium pensylvanicum), sorghum, corn, soybean, sugar beet, rice, wheat, purple nutsedge (Cyperus rotundus) tubers, and in certain cases, cotton were planted and treated pre-emergence with the test chemicals dissolved in a non-phytotoxic solvent. At the same time, these crop and weed species, along with cotton and bush bean, were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings are based on a numerical scale extending from 0=no injury, to 10=complete kill. The accompanying descriptive symbols have the following meanings:

C=chlorosis/necrosis;
E=emergence inhibition;
G=growth retardation;
H=formative effects;
L=lodging;
U=unusual pigmentation;
X=axillary stimulation; and
6Y=abscised flowers or buds.

TABLE IV

| Rate (kg/ha) | 0.05 |
|---|---|
| POSTEMERGENCE | |
| Morningglory | 3G |
| Cocklebur | 4C,8H |
| Velvetleaf | 2C |
| Nutsedge | 0 |
| Crabgrass | 0 |
| Barnyardgrass | 0 |
| Cheatgrass | 0 |
| Wild Oats | 0 |
| Wheat | 0 |
| Corn | 0 |
| Soybean | 1H |
| Rice | 8G |
| Sorghum | 2C,7H |
| Sugar Beets | 3C,7G |
| Cotton | 0 |
| PREEMERGENCE | |
| Morningglory | 4G |
| Cocklebur | 0 |
| Velvetleaf | 0 |
| Nutsedge | 0 |
| Crabgrass | 0 |

TABLE IV-continued

| | Rate (kg/ha) | 0.05 |
|---|---|---|
| | Barnyardgrass | 0 |
| | Cheatgrass | 0 |
| | Wild Oats | 0 |
| | Wheat | 0 |
| | Corn | 6G |
| | Soybean | 0 |
| | Rice | 7G |
| | Sorghum | 8H |
| | Sugar Beets | 7G |
| | Cotton | 0 |

What is claimed is:

1. A compound of the formula:

$$J-SO_2NHC(=W)-N(R)-A$$

wherein
J is [structures $J_1$, $J_2$, $J_3$, $J_5$, $J_6$, $J_7$, $J_9$, $J_{12}$, $J_{22}$, $J_{23}$, $J_{24}$, $J_{25}$, $J_{26}$];

n is 0, 1 or 2;
W is O or S;
$W_1$ is O or S;
R is H or $CH_3$;
$R_1$ is H, F, Cl, Br, $CH_3$, $OCH_3$, $CF_3$, $SCH_3$ or $OCF_2H$;
$R_2$ is H or $C_1$-$C_4$ alkyl;
$R_3$ and $R_4$ are independently H, $C_1$-$C_4$ alkyl, Cl or Br;
$R_5$ is H or $CH_3$;
$R_6$ is H or $CH_3$;
$R_7$ is H or $CH_3$;
A is

[pyrimidine structure with cyclopropyl, Z, Y substituents]

Y is
$CH_3$, $CH_2CH_3$, $OCH_3$, $OCH_2CH_3$, $CH_2OCH_3$, $OCF_2H$, $SCF_2H$, $OCH_2CF_3$, $CF_3$, $OCH_2CH=CH_2$, $OCH_2C\equiv CH$, $NHCH_3$, $N(CH_3)_2$ or $CH(OCH_3)_2$; and
Z is CH provided that
 (a) when W is S, then R is H;
 (b) the total number of carbon atoms in $R_3$ and $R_4$ is less than or equal to 4;
 (c) when $R_5$ is $CH_3$, then n is 0; and
 (d) when J is $J_{24}$, then $R_4$ and $R_5$ are not both H and $R_4$ is not Cl or Br;
and their agriculturally suitable salts.

2. Compounds of claim 1 where W is O, $R_3$ and $R_4$ are independently H or $C_1$-$C_3$ alkyl and $R_1$ is bonded to the ortho or metal position of the ring relative to the sulfonylurea moiety.

3. Compounds of claim 2 wherein $R_1$ is H, F, Cl, Br, $CH_3$, $OCH_3$, $CF_3$ or $SCH_3$ and R is H.

4. Compounds of claim 3 where $R_1$ is H, F, Cl, $CH_3$, $OCH_3$ or $SCH_3$, $R_5$ is H and Y is $CH_3$, $OCH_3$ or $CH_2OCH_3$.

5. Compounds of claim 4 where J is $J_1$.
6. Compounds of claim 4 where J is $J_2$.
7. Compounds of claim 4 where J is $J_3$.
8. Compounds of claim 4 where J is $J_5$.
9. Compounds of claim 4 where J is $J_6$.
10. Compounds of claim 4 where J is $J_7$.
11. Compounds of claim 4 where J is $J_9$.

12. Compounds of claim 4 where J is $J_{12}$.
13. Compounds of claim 4 where J is $J_{22}$.
14. Compounds of claim 4 where J is $J_{23}$.
15. Compounds of claim 4 where J is $J_{24}$.
16. Compounds of claim 4 where J is $J_{25}$.
17. Compounds of claim 4 where J is $J_{26}$.
18. A composition suitable for controlling the growth of undesired vegetation which comprises an effective amount of a compound of claim 1 and at least one of the following: surfactant, solid or liquid inert diluent.
19. A composition suitable for controlling the growth of undesired vegetation which comprises an effective amount of a compound of claim 2 and at least one of the following: surfactant, solid or liquid inert diluent.
20. A composition suitable for controlling the growth of undesired vegetation which comprises an effective amount of a compound of claim 3 and at least one of the following: surfactant, solid or liquid inert diluent.
21. A composition suitable for controlling the growth of undesired vegetation which comprises an effective amount of a compound of claim 4 and at least one of the following: surfactant, solid or liquid inert diluent.
22. A composition suitable for controlling the growth of undesired vegetation which comprises an effective amount of a compound of claim 5 and at least one of the following: surfactant, solid or liquid inert diluent.
23. A method for controlling the growth of undesired vegetation which comprises applying to the locus to be protected an effective amount of a compound of claim 1.
24. A method for controlling the growth of undesired vegetation which comprises applying to the locus to be protected an effective amount of a compound of claim 2.
25. A method for controlling the growth of undesired vegetation which comprises applying to the locus to be protected an effective amount of a compound of claim 3.
26. A method for controlling the growth of undesired vegetation which comprises applying to the locus to be protected an effective amount of a compound of claim 4.
27. A method for controlling the growth of undesired vegetation which comprises applying to the locus to be protected an effective amount of a compound of claim 5.

* * * * *